United States Patent [19]
Dodge et al.

[11] Patent Number: 5,912,117
[45] Date of Patent: Jun. 15, 1999

[54] METHOD FOR DIAGNOSIS OF LYME DISEASE

[75] Inventors: Deborah E. Dodge, Albany; Thomas J. White, Oakland, both of Calif.

[73] Assignee: Roche Molecular Systems, Inc., Branchburg, N.J.

[21] Appl. No.: 07/923,871

[22] PCT Filed: Mar. 7, 1991

[86] PCT No.: PCT/US91/01574

§ 371 Date: Oct. 9, 1992

§ 102(e) Date: Oct. 9, 1992

[87] PCT Pub. No.: WO91/14002

PCT Pub. Date: Sep. 19, 1991

Related U.S. Application Data

[63] Continuation-in-part of application No. 07/489,676, Mar. 7, 1990, abandoned.

[51] Int. Cl.$^6$ ................................................ C12Q 1/68
[52] U.S. Cl. ........................ 435/6; 435/91.2; 435/810; 436/501; 536/23.1; 536/24.1; 536/24.3; 536/24.31; 536/24.32; 536/24.33; 935/77; 935/78
[58] Field of Search ..................... 435/6, 810, 91.2; 436/501; 536/23.1, 24.1, 24.3–24.33; 935/77, 78

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,800,159 | 1/1989 | Mullis et al. | 435/172.3 |
| 4,851,330 | 7/1989 | Kohne | 435/6 |
| 4,888,276 | 12/1989 | Shelburne | 435/7 |
| 4,965,188 | 10/1990 | Mullis et al. | 435/6 |
| 5,043,272 | 8/1991 | Hartley | 435/91 |
| 5,401,631 | 3/1995 | Lane et al. | 435/6 |
| 5,466,577 | 11/1995 | Weisburg | 435/6 |

FOREIGN PATENT DOCUMENTS

| | | |
|---|---|---|
| 0421725 | 4/1991 | European Pat. Off. |
| 8402721 | 7/1984 | WIPO |
| 9119814 | 12/1991 | WIPO |

OTHER PUBLICATIONS

*Bethesda Research Labs. Catalogue* (publ. 1985 by Bethesda Res. Labs., Gaithersburg, MD, USA) pp. 52 and 53.
Sommer et al. (1989) Nucleic Acids Res., vol. 17, No. 16, p. 6749.
Weisburg et al. (1991) J. of Bacteriology, vol. 173, No. 2, pp. 697–703.
Brosius et al. (1978) Proc. Natl Acad Sci (USA), vol. 75, No. 1, pp. 4801–4805.
Barbour (1989) Ann Intern Med 110:501.
Dattwyler, et al. (1988), N. Engl. J. Med 319:1441.
Byrne, et al. (1988) Nuc Acids Res 16:4165.
Schwan, et al. (1989) J Clin Microbiol 27:1734.
Rosa and Schwan (1989) J Infect Diseases 160:1018.
Saiki, et al. (1985) Science 230:1350.
Van Eys, et al. (1989) J Clin Mcrobiol 27:2258.

*Primary Examiner*—Ardin H. Marschel
*Attorney, Agent, or Firm*—George W. Johnston; Dennis P. Tramaloni; Doug Petry

[57] ABSTRACT

Methods and reagents are provided for amplifying and detecting target nucleic acid sequences in a sample suspected of containing Borrelia spirochetes using the polymerase chain reaction (PCR) process. The PCR process employs primers and probes which are derived from the 16S ribosomal RNA gene of *Borrelia burgdorferi* and *Borrelia hermsii*.

13 Claims, 10 Drawing Sheets

FIG. 1A

SEQ ID NO: 13    TAGAGGGGGGTAGAATTCCAGGTGTAGCGGTGAAATGCGTAGAGATCTGG

SEQ ID NO: 13    AGGAATACCCGGTGGCGAAGGCGGCCCCCCTGGACGAAGACTGACGCTCAGG

SEQ ID NO: 13    TGCCGAAAGCGTGGGGAGCAAACAGGATTAGATACCCTGGTAGTCCACGCC

SEQ ID NO: 13    GTAAACGATGTCGACTTGGAGGTTGTGCCCTTGAGGCGTGGCTTCCGGAG

SEQ ID NO: 13    CTAACGCGTTAAGTCGACCGCCTGGGGAGTACGGCCGCAAGGTTAAAACT

SEQ ID NO: 13    CAAATGAATTGACGGGGCCCGCACAAGCGGTGGAGCATGTGGTTTAATT

FIG. 1B

```
SEQ ID NO: 37                                                              GTATA GGANGATAGTT
SEQ ID NO: 13   CGATGCAACGCGAAGAACCTTACCTGGTCTCTTGACATCCAC GGAAGTT  TTC

SEQ ID NO: 37   AGAGATAATTAT TCCCCGNNTGGGN CTAT ATACAGGTGCTGCATGGTTG
SEQ ID NO: 13   AGAGATCAGAATGTGCCT TC  GGGAACCGTGAGACAGGTGCTGCATGGCTG

SEQ ID NO: 37   TNGTCAGCTCGTCGTGCTGTGAGGTGTTGGGTTAAGTCCCG AACGAG G AA
SEQ ID NO: 13   TCGTCAGCTCGTCGTGTTGTGAAATGTTGGGTTAAGTCCCCGCAACGAGCGCAA

|----- DD06 -------|
SEQ ID NO: 37   CCCTTGTTATCTGTTACCAGCATGTAATGGTGGGGA CTCAGATAAGACTG
SEQ ID NO: 13   CCCTTATCCCTTTGTTGCCAGCCG GTCC  GGCCGGGAACTCAAAGGAGACTG

SEQ ID NO: 37   C AGGTTGATAAG TCGGAGGAAGGTGAGGATGACGTCAAATCATCATGGC
SEQ ID NO: 13   CCAG T GATAAACT GGAGGAAGGTGGGGATGACGTCAAGTCATCATGGC

SEQ ID NO: 37   CCTTATGTCCTGGGCTACACACGTGCTACACAATGGC CTGTACAAAGCG
SEQ ID NO: 13   CCTTACGACCAGGGCTACACACGTGCTACAATGGCGCA TACAAAGAGAAG
```

FIG. 1C

```
SEQ ID NO: 13    CGACCTCGCGAGAGCAAGCGGACCTCATAAAGTGCGTCGTAGTCCGATT

SEQ ID NO: 13    GGAGTCTGCAACTCGACTCCATGAAGTCGGAATCGCTAGTAATCGTGGAT

|----- DG73 -------|
SEQ ID NO: 13    CAGAATGCCACGGTTGAATACGTTCCCGGCCTTGTACACACCGCCCGTCA

|------- DD03 -------|          |----- DD04 --
                  ** * *** *  * ****   *    * ** * ** **
SEQ ID NO: 38    CACCC GAGTTGAGGATACCC   GAAGCTAT TATTCT AACCCGTAAGGGA
SEQ ID NO: 13    CACCATGGGA GTGGGTTGCAAAAGAAG TAGGTAG CTTAACCT TC GGGA

------|   |----- DD02 -------|
                  ** * *  **** ** ****   *  * **  *  * **
SEQ ID NO: 38    GGAAGGTATTTAAGGTA TGTTT AGTGAGGGGGTGAA
SEQ ID NO: 13    GGGCGCT TACCACTTTGTGATTCA TGACTGGGGTGAAGTCGTAACAAGGT

|----- DG74 ------|
SEQ ID NO: 13    AACCGTAGGGGAACCTGCGGTTGGATCACCTCCTTA
```

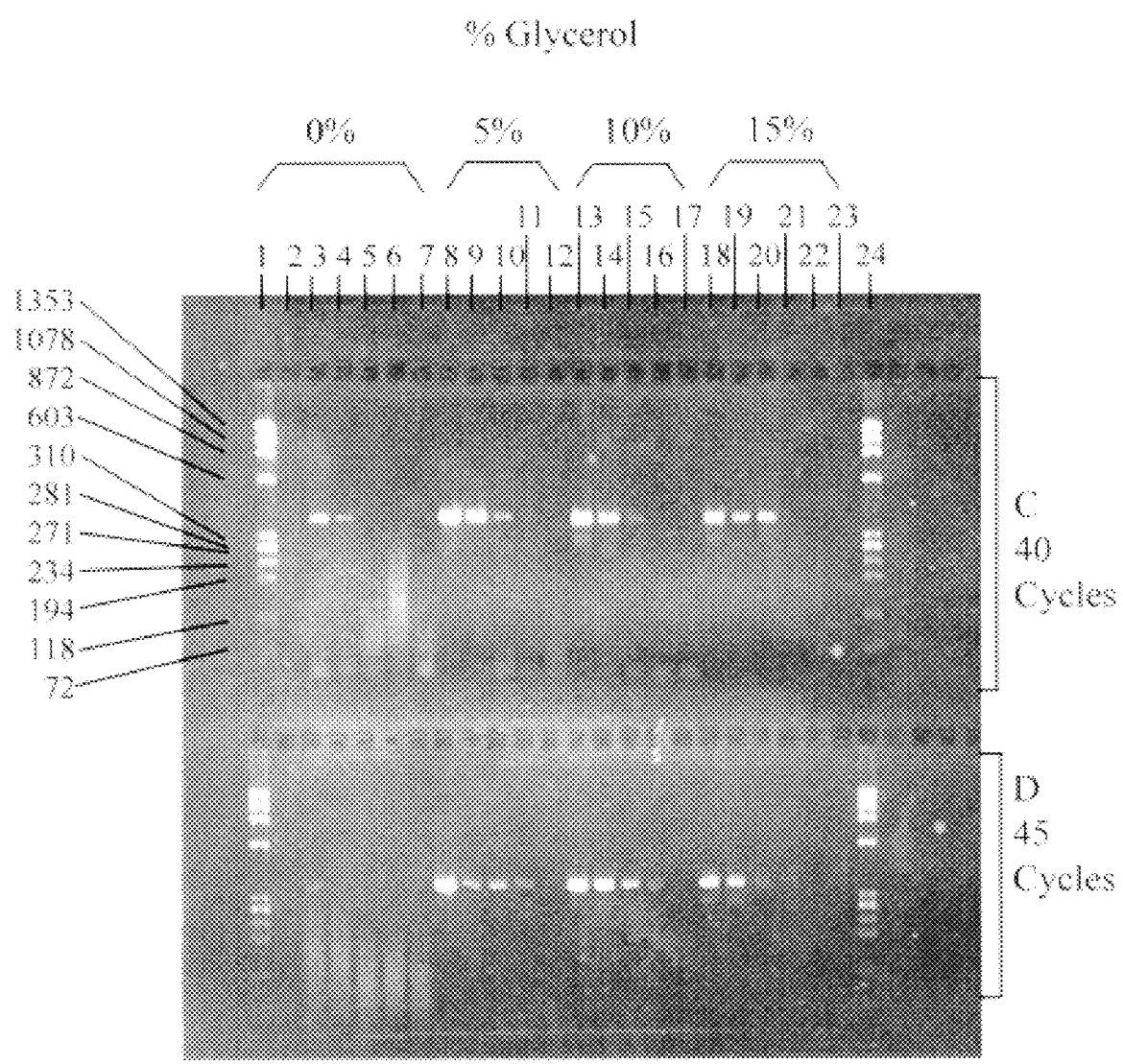

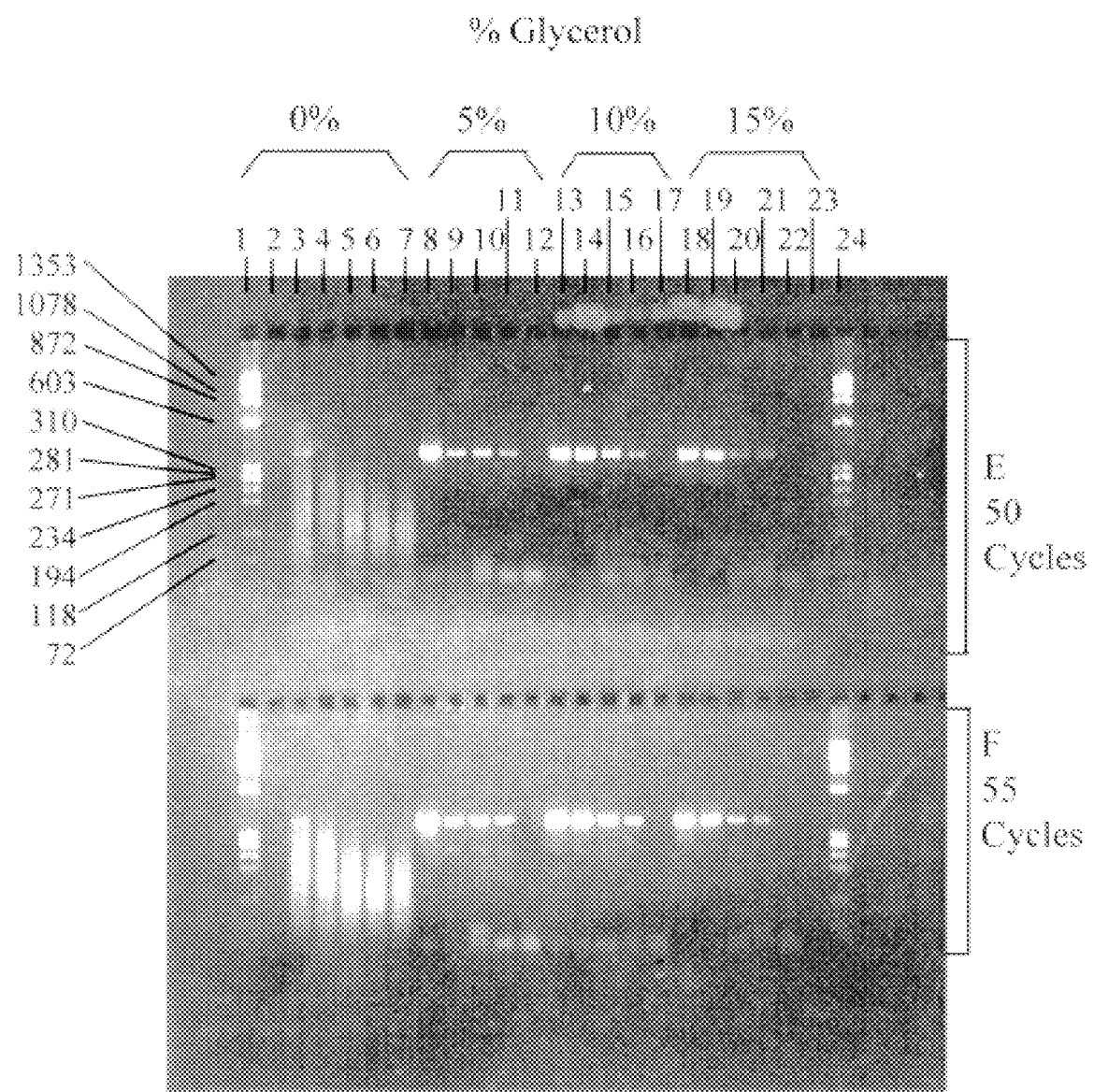

```
                                 DD06                      DD27
B. burg (SEQ ID NO: 35)  ATCTGTTACCAGCATGTAATGGTGGGGACTCAGATAAGACTGCNNGNTNGATAAGTCGGAGG   62
B. herm (SEQ ID NO: 36)  ATCTGTTACCAGCATGTAATGATGGGGACTCAGACGAGACTGCNNGNTNGATAAG CCGAG   60
            burg/herm    .....................A............CG.......NN.N.N...... .C...

B. burg    AAGGTGAGGATGACGTCAAATCATCATGGCCCTTATGTCCTGGGCTACACACGTGCTACA   122
B. herm    AAGGTGAGGATGACGTCAAATCATCATGGCCCTTATGTCCTGGGCTACACACGTGCTACA   120
burg/herm  ............................................................

DD25
B. burg    ATGGCCTGTACAAAGCGACAGAACAGTGATGTGAAGCAAAACGCATAAAGCAGGTCTCAG   182
B. herm    ATGGCCTGTACAAAGCGATGAAACAGTGATGTGAAGCAAAACGCATAAAGCAGGTCTCAG   180
burg/herm  ..................TGA.......................................

B. burg    TCCGGATTGAAGTCTGAAACTCGACTTCATGAAGTTGGAATCGCTAGTAATCGTATATCA   242
B. herm    TCCAGATTGAAGTCTGAAACTCGACTTCATGAAGTTGGAATCGCTAGTAATCGTATATCA   240
burg/herm  ...A........................................................

B. burg    GAATGATACGGTGAATACGTTCTCGGGCCTTGTACACACCGCCCGTCACACCACCCGAGT   302
B. herm    GAATGATACGGTGAATACGTTCTCGGGCCTTGTACACACCGCCCGTCACACCACCCGAGT   300
burg/herm  ............................................................

DD04                 DD02
B. burg    TGAGGATACCCGAAGCTATTATTCTAACCCGTAAGGGAGGAAGGTATTTAAGGTATGTTT   362
B. herm    TGAGGATACCCGAAGCTATTATTCTAACCCGCAAGGGAGGAAGGTATCTAAGGTATGTTT   360
burg/herm  ...............................C...............C............

B. burg    AGTGAGGG                                                       370
B. herm    AGTGAGGG                                                       368
burg/herm  ........
```

FIG. 6

SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
      (A) LENGTH: 498 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: unsure
      (B) LOCATION: complement (35..36)

(ix) FEATURE:
      (A) NAME/KEY: unsure
      (B) LOCATION: complement (41)

(ix) FEATURE:
      (A) NAME/KEY: unsure
      (B) LOCATION: complement (67)

(ix) FEATURE:
      (A) NAME/KEY: unsure
      (B) LOCATION: complement (164..165)

(ix) FEATURE:
      (A) NAME/KEY: unsure
      (B) LOCATION: complement (167)

(ix) FEATURE:

```
            (A) NAME/KEY: unsure
            (B) LOCATION: complement (169)

(xi) SEQUENCE DESCRIPTION: SEQ ID NO:1:

GTATAGGAAG ATAGTTAGAG ATAATTATTC CCCGNNTGGG NCTATATACA GGTGCTGCAT      60

GGTTGTNGTC AGCTCGTGCT GTGAGGTGTT GGGTTAAGTC CCGAACGAGG AACCCTTGTT     120

ATCTGTTACC AGCATGTAAT GGTGGGGACT CAGATAAGAC TGCNNGNTNG ATAAGTCGGA     180

GGAAGGTGAG GATGACGTCA AATCATCATG GCCCTTATGT CCTGGGCTAC ACACGTGCTA     240

CAATGGCCTG TACAAAGCGA CAGAACAGTG ATGTGAAGCA AAAACGCATA AAGCAGGTCT     300

CAGTCCGGAT TGAAGTCTGA AACTCGACTT CATGAAGTTG GAATCGCTAG TAATCGTATA     360

TCAGAATGAT ACGGTGAATA CGTTCTCGGG CCTTGTACAC ACCGCCCGTC ACACCACCCG     420

AGTTGAGGAT ACCCGAAGCT ATTATTCTAA CCCGTAAGGG AGGAAGGTAT TTAAGGTATG     480

TTTAGTGAGG GGGGTGAA                                                   498

(2) INFORMATION FOR SEQ ID NO:2:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

TCCATACAAA TCACTCCC                                                    18

(2) INFORMATION FOR SEQ ID NO:3:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

CACCCGAGTT GAGGATACC                                                   19

(2) INFORMATION FOR SEQ ID NO:4:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

CCCGTAAGGG AGGAAGGTAT                                                  20
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

ATAGTTAGAG ATAATTATTC                                            20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

ATCTGTTACC AGCATGTAAT                                            20

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

CGTGCTACAA TGGCCTG                                                17

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

GGAAGATAGT TAGAGATAAT TATTC                                    25

(2) INFORMATION FOR SEQ ID NO:9:

(i) SEQUENCE CHARACTERISTICS:

(A) LENGTH: 26 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

CTTGTTATCT GTTACCAGCA TGTAAT                                              26

(2) INFORMATION FOR SEQ ID NO:10:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

TATCTGTTAC CAGCATGTAA T                                                   21

(2) INFORMATION FOR SEQ ID NO:11:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

ACACACGTGC TACAA                                                          15

(2) INFORMATION FOR SEQ ID NO:12:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:12:

CAGATAAGAC TGCCGGTGAT AAGTC                                               25

(2) INFORMATION FOR SEQ ID NO:13:

(i) SEQUENCE CHARACTERISTICS:
            (A) LENGTH: 882 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:13:

| | | | | | | |
|---|---|---|---|---|---|---|
| TAGAGGGGGG | TAGAATTCCA | GGTGTAGCGG | TGAAATGCGT | AGAGATCTGG | AGGAATACCG | 60 |
| GTGGCGAAGG | CGGCCCCCTG | GACGAAGACT | GACGCTCAGG | TGCGAAAGCG | TGGGGAGCAA | 120 |
| ACAGGATTAG | ATACCCTGGT | AGTCCACGCC | GTAAACGATG | TCGACTTGGA | GGTTGTGCCC | 180 |
| TTGAGGCGTG | GCTTCCGGAG | CTAACGCGTT | AAGTCGACCG | CCTGGGGAGT | ACGGCCGCAA | 240 |
| GGTTAAAACT | CAAATGAATT | GACGGGGGCC | CGCACAAGCG | GTGGAGCATG | TGGTTTAATT | 300 |
| CGATGCAACG | CGAAGAACCT | TACCTGGTCT | TGACATCCAC | GGAAGTTTTC | AGAGATCAGA | 360 |
| ATGTGCCTTC | GGGAACCGTG | AGACAGGTGC | TGCATGGCTG | TCGTCAGCTC | GTGTTGTGAA | 420 |
| ATGTTGGGTT | AAGTCCCGCA | ACGAGCGCAA | CCCTTATCCT | TTGTTGCCAG | CGGTCCGGCC | 480 |
| GGGAACTCAA | AGGAGACTGC | CAGTGATAAA | CTGGAGGAAG | GTGGGGATGA | CGTCAAGTCA | 540 |
| TCATGGCCCT | TACGACCAGG | GCTACACACG | TGCTACAATG | GCGCATACAA | AGAGAAGCGA | 600 |
| CCTCGCGAGA | GCAAGCGGAC | CTCATAAAGT | GCGTCGTAGT | CCGGATTGGA | GTCTGCAACT | 660 |
| CGACTCCATG | AAGTCGGAAT | CGCTAGTAAT | CGTGGATCAG | AATGCCACGG | TTGAATACGT | 720 |
| TCCCGGGCCT | TGTACACACC | GCCCGTCACA | CCATGGGAGT | GGGTTGCAAA | AGAAGTAGGT | 780 |
| AGCTTAACCT | TCGGGAGGGC | GCTTACCACT | TTGTGATTCA | TGACTGGGGT | GAAGTCGTAA | 840 |
| CAAGGTAACC | GTAGGGGAAC | CTGCGGTTGG | ATCACCTCCT | TA | | 882 |

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:14:

GGGCATTCCC TCCTTCCATA                                                       20

(2) INFORMATION FOR SEQ ID NO:15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:15:

TAACCCGTAA GGGAGGA                                                          17

(2) INFORMATION FOR SEQ ID NO:16:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:16:

ATTGGGCATT CCCTCCT                                              17

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

TCCATACAAA TCACTCCGTC CACTG                                     25

(2) INFORMATION FOR SEQ ID NO:18:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

GTCCAGCATC TGTTACCAGC ATGTAAT                                   27

(2) INFORMATION FOR SEQ ID NO:19:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:19:

ATTCCCTCCT TCCATA                                               16

(2) INFORMATION FOR SEQ ID NO:20:

(i) SEQUENCE CHARACTERISTICS:
        (A) LENGTH: 15 base pairs
        (B) TYPE: nucleic acid
        (C) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:20:

GTGCTACAAT GGCCT                                                         15

(2) INFORMATION FOR SEQ ID NO:21:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:21:

AACCCGTAAG GGAGGAAGGT ATTTAAG                                             27

(2) INFORMATION FOR SEQ ID NO:22:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:22:

TTGGGCATTC CCTCCTTCCA TAAATTC                                             27

(2) INFORMATION FOR SEQ ID NO:23:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:23:

TTCTAACCCG TAAGGGAGGA                                                    20

(2) INFORMATION FOR SEQ ID NO:24:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:24:

AAGATTGGGC ATTCCCTCCT                                                          20

(2) INFORMATION FOR SEQ ID NO:25:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:25:

ACAAGCGGTG GAGCATGTGG                                                          20

(2) INFORMATION FOR SEQ ID NO:26:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:26:

GGTTAAGTCC CGCAACGAGC GC                                                       22

(2) INFORMATION FOR SEQ ID NO:27:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:27:

TACGTTCCCG GGCCTTGTAC                                                          20

(2) INFORMATION FOR SEQ ID NO:28:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:28:

AGGAGGTGAT CCAACCGACA                                                          20

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:29:

AAAGCGACAG AACAGTGA                                                            18

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:30:

GGACTCAGAT AAGACTGC                                                            18

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_difference
        (B) LOCATION: replace(5, "N")
        (D) OTHER INFORMATION: /standard_name= "base substitution"
            /note= "At position 5 the base may be either T or
            C"

(ix) FEATURE:
        (A) NAME/KEY: misc_difference
        (B) LOCATION: replace(21, "N")
        (D) OTHER INFORMATION: /standard_name= "base substitution"
            /note= "At position 21 the base may be T, C or
            absent"

(xi) SEQUENCE DESCRIPTION: SEQ ID NO:31:

CCCGNAAGGG AGGAAGGTAT N                                                        21

(2) INFORMATION FOR SEQ ID NO:32:

(i) SEQUENCE CHARACTERISTICS:
        (A) LENGTH: 12 base pairs (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_difference
            (B) LOCATION: replace(4, "N")
            (D) OTHER INFORMATION: /standard_name= "base substitution"
                /note= "At position 4 the base may be T or C"

(xi) SEQUENCE DESCRIPTION: SEQ ID NO:32:

CCGNAAGGGA GG                                                                  12

(2) INFORMATION FOR SEQ ID NO:33:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:33:

CCCGCAAGGG AGGAAGGTAT C                                                        21

(2) INFORMATION FOR SEQ ID NO:34:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:34:

ATATACCTTC CTCCCTTTCG GG                                                       22

(2) INFORMATION FOR SEQ ID NO:35:

(i) SEQUENCE CHARACTERISTICS:
            (A) LENGTH: 370 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:35:

ATCTGTTACC AGCATGTAAT GGTGGGGACT CAGATAAGAC TGCNNGNTNG ATAAGTCGGA      60

GGAAGGTGAG GATGACGTCA AATCATCATG GCCCTTATGT CCTGGGCTAC ACACGTGCTA     120

CAATGGCCTG TACAAAGCGA CAGAACAGTG ATGTGAAGCA AAACGCATAA AGCAGGTCTC     180

AGTCCGGATT GAAGTCTGAA ACTCGACTTC ATGAAGTTGG AATCGCTAGT AATCGTATAT     240

CAGAATGATA CGGTGAATAC GTTCTCGGGC CTTGTACACA CCGCCCGTCA CACCACCCGA     300

GTTGAGGATA CCCGAAGCTA TTATTCTAAC CCGTAAGGGA GGAAGGTATT TAAGGTATGT     360

TTAGTGAGGG                                                            370

(2) INFORMATION FOR SEQ ID NO:36:

(i) SEQUENCE CHARACTERISTICS:
            (A) LENGTH: 368 base pairs
            (B) TYPE: nucleic acid
            (C) STRANDEDNESS: single (D) TOPOLOGY: linear (ii) MOLECULE TYPE: DNA (genomic)

(xi) SEQUENCE DESCRIPTION: SEQ ID NO:36:

ATCTGTTACC AGCATGTAAT GATGGGGACT CAGACGAGAC TGCNNGNTNG ATAAGCCGAG      60

AAGGTGAGGA TGACGTCAAA TCATCATGGC CCTTATGTCC TGGGCTACAC ACGTGCTACA     120

ATGGCCTGTA CAAAGCGATG AAACAGTGAT GTGAAGCAAA ACGCATAAAG CAGGTCTCAG     180

TCCAGATTGA AGTCTGAAAC TCGACTTCAT GAAGTTGGAA TCGCTAGTAA TCGTATATCA     240

GAATGATACG GTGAATACGT TCTCGGGCCT TGTACACACC GCCCGTCACA CCACCCGAGT     300

TGAGGATACC CGAAGCTATT ATTCTAACCC GCAAGGGAGG AAGGTATCTA AGGTATGTTT     360

AGTGAGGG                                                              368

(2) INFORMATION FOR SEQ ID NO:37:

(i) SEQUENCE CHARACTERISTICS:
        (A) LENGTH: 258 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

GTATAGGANG ATAGTTAGAG ATAATTATTC CCCGNNTGGG NCTATATACA GGTGCTGCAT      60

GGTTGTNGTC AGCTCGTGCT GTGAGGTGTT GGGTTAAGTC CCGAACGAGG AACCCTTGTT    120

ATCTGTTACC AGCATGTAAT GGTGGGGACT CAGATAAGAC TGCAGGTTGA TAAGTCGGAG    180

GAAGGTGAGG ATGACGTCAA ATCATCATGG CCCTTATGTC CTGGGCTACA CACGTGCTAC    240

AATGGCCTGT ACAAAGCG                                                  258

(2) INFORMATION FOR SEQ ID NO:38:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

CACCCGAGTT GAGGATACCC GAAGCTATTA TTCTAACCCG TAAGGGAGGA AGGTATTTAA      60

GGTATGTTTA GTGAGGGGGG TGAA                                            84

METHOD FOR DIAGNOSIS OF LYME DISEASE

CROSS-REFERENCE TO RELATED APPLICATIONS

This is the U.S. National Phase of International Application No. PCT/US91/01574, filed Mar. 7, 1991, which is a continuation-in-part application of U.S. Ser. No. 07/489,676 filed Mar. 7, 1990, now abandoned which is incorporated herein by reference.

TECHNICAL FIELD

The invention relates generally to methods and reagents for the detection of Lyme disease, a multisystem bacterial infection transmitted by Ixodid ticks. More particularly, the methods employ polymerase chain reaction to amplify genomic nucleic acid sequences specific to the etiologic agent of Lyme disease, Borrelia burgdorferi.

BACKGROUND OF THE INVENTION

Lyme disease is a complex multisystem disorder caused by the tick-borne spirochete Borrelia buradorferi. This disease has three clinical stages that can overlap or occur alone: stage one—early disease, including a characteristic expanding skin lesion (erythema chronicum migrans) and constitutional flu-like symptoms; stage two—cardiac and neurological disease; and stage three—arthritis and chronic neurological syndromes.

Presently, the incidence of reported Lyme disease is increasing, which is probably due to improved awareness and recognition of the disease, as well as to an actual increase in incidence and geographic spread. B. burgdorferi can be isolated from blood or skin biopsies taken from acutely ill patients, but the yield is low and the procedures are difficult. Serologic testing for antibodies using an enzyme-linked immunosorbent assay (ELISA) or indirect immunofluorescence assay (IFA) is the standard method used to confirm a clinical diagnosis, but current tests are poorly standardized, and false-negative or false-positive results can occur (Barbour, (1989) Ann Intern Med 110:501). In addition to misdiagnosis caused by lack of standardization of serologic testing, cross-reactivity with Treponema and with other Borrelia may occur. Patients with stage one or two disease may be seronegative because it may take as long as three to six months after exposure for antibodies to become detectable with currently available tests. Patients who develop later stages of the illness may occasionally be seronegative if they were treated acutely with antibiotics (Dattwyler et al., (1988) N Engl J Med 319:1441). Previously untreated patients with a late stage of the disease are, apparently, almost always seropositive.

The use of specific polynucleotide sequences as probes for the recognition of infectious agents is becoming a valuable alternative to problematic immunological identification assays. For example, PCT publication WO84/02721, published Jul. 19, 1984 describes the use of nucleic acid probes complementary to targeted nucleic acid sequences composed of ribosomal RNA, transfer RNA, or other RNA in hybridization procedures to detect the target nucleic acid sequence. While the assay may provide greater sensitivity and specificity than known DNA hybridization assays, hybridization procedures which require the use of a complementary probe are generally dependent upon the cultivation of a test organism and are, therefore, unsuitable for rapid diagnosis.

Polymerase chain reaction (PCR) is a powerful technique that can be used for the detection of small numbers of pathogens whose in vitro cultivation is difficult or lengthy, or as a substitute for other methods which require the presence of living specimens for detection. In its simplest form, PCR is an in vitro method for the enzymatic synthesis of specific DNA sequences, using two oligonucleotide primers that hybridize to opposite strands and flank the region of interest in the target DNA. A repetitive series of cycles involving template denaturation, primer annealing, and the extension of the annealed primers by DNA polymerase results in the exponential accumulation of a specific fragment whose termini are defined by the 5' ends of the primers. PCR reportedly is capable of producing a selective enrichment of a specific DNA sequence by a factor of $10^9$. The PCR method is described in Saiki et al., (1985) Science 230:1350 and is the subject of U.S. Pat. Nos. 4,683,195; 4,683,202; 4,800,159; and 4,965,188. This method has been used to detect the presence of the aberrant sequence in the beta-globin gene which is related to sickle cell anemia (Saiki et al., (1985) supra) and the human immunodeficiency virus (HIV) RNA (Byrne et al., (1988) Nuc Acids Res 16:4165). However, before the method can be used, enough of the nucleotide sequence of the disease-associated polynucleotide must be known to design primers for the amplification, and to design probes specific enough to detect the amplified product.

Both genomic and plasmid DNA sequences have been used for the identification of Borrelia, but neither of these methods have been shown to detect all Borrelia burgdorferi isolates. Schwan et al., [(1989) J Clin Microbiol 27:1734 and (1988) Ann NY Acad Sci 539:419] use nucleic acid hybridization probes derived from the 49 kilobase linear plasmid of B. burgdorferi for the detection and identification of B. burgdorferi from a number of other Borrelia species in the United States. A nucleic acid probe containing the 5' portion of the variable major protein 7 (vmp 7) of B. hermsii (the causative agent of tick-borne relapsing fever) was also employed in these studies.

One of the inherent limitations of this assay is its dependency on the identification of plasmid DNA. Such identification procedures are inherently unreliable given that plasmids, over time, are unstable in cultured spirochetes or may be absent from some natural isolates of the pathogen or clinical specimens.

Rosa and Schwan (1989) J Infect Dis 160(6):1018 used PCR to amplify a target selected from randomly cloned B. burgdorferi DNA. While the specificity of the PCR assay suggested a utility for this technique, not all B. burgdorferi isolates were detected. Since it is not known currently whether Lyme disease is caused by all isolates of B. burgdorferi, it is essential for accurate diagnosis to demonstrate that all isolates will be detected in any given assay system. Furthermore, their system is not sensitive enough to detect the pathogen in clinical or biological specimens.

In light of current limitations for the serological identification of Lyme disease, it would be desirable to provide a rapid and sensitive procedure for the detection of B. burgdorferi in a clinical sample suspected of containing the spirochete. It would also be desirable to develop reagents that are useful for detecting all geographical isolates of B. burgdorferi.

BRIEF DESCRIPTION OF THE DRAWINGS

FIGS. 1A, FIG. 1B, and FIG. 1C show a comparison of a partial region of the nucleotide sequences of the 16S rRNA genes from *E. coli* (- SEQ ID No: 13) aligned for maximum identity with *B. burgdorferi* (- SEQ ID No: 38 and SEQ. ID No. 39). The region shown corresponds to nucleotides 661 through 1542, numbered in accordance with the nucleotide sequence of the *E. coli* 16S rRNA gene. The nucleotides marked by asterisk superscripts are heterogeneous between the two bacteria.

FIG. 6 shows a comparison of a partial region of the nucleotide sequences of the 16S rRNA genes from *B. burgdorferi* (top line-SEQ ID No: 35) aligned for maximum identify with *B. hermsii* (middle line-SEQ ID No: 36). The bottom line indicates differences in specific nucleotides.

DISCLOSURE OF THE INVENTION

Figure 2:
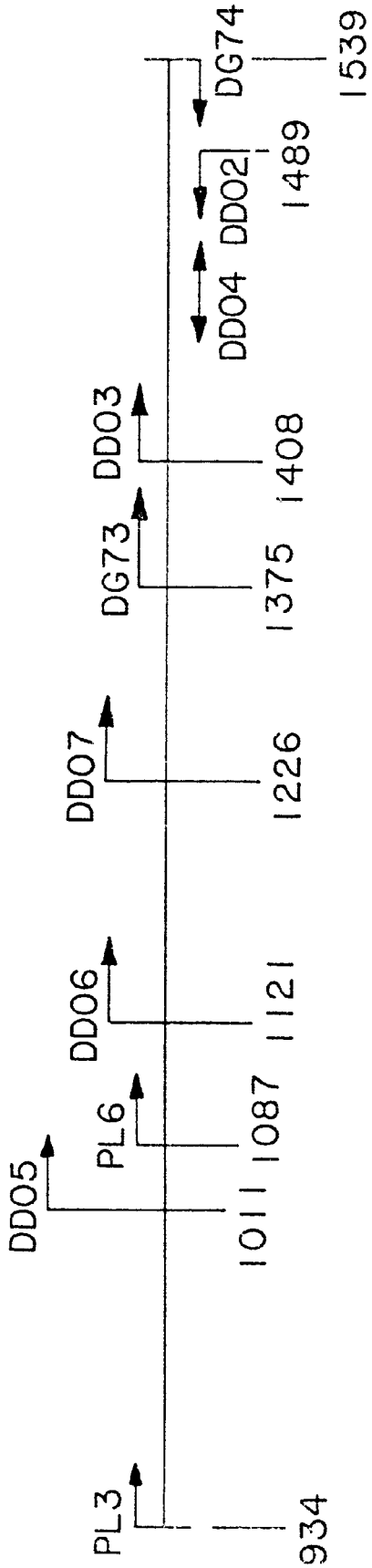
FIG. 2 is a partial linear representation of the 16S rRNA gene shown in FIG. 1A, FIG. 1B, and FIG 1C. The various primers are designated therein with respect to their point of initiation.

The present invention pertains to methods and reagents useful for the detection of Borrelia species, particularly those species known to be the etiologic agents of Lyme disease and tick-borne relapsing fever. Detection of the presence of the agent is based upon the detection of the gene coding for the 16S ribosomal RNA (rRNA), as well as fragments or transcripts derived therefrom, in biological samples. The method entails amplifying a target region from genomic DNA or from a reverse transcript of Borrelia 16S rRNA and detecting the amplified polynucleotide by hybridization. The method utilizes primers and probes which are available due to the information provided in portions of the 16S rRNA gene sequence.

Studies of the structure of the 16S rRNA gene sequence from bacterial species suggest that there are regions of conserved sequence among these genes. These conserved sequences allow the creation of primers which may be universal in their application for amplification of target regions of the genus Borrelia. Identification of the species is then accomplished utilizing a probe specific for the species; identification of *Borrelia burgdorferi* is accomplished utilizing a probe specific for this species, the sequence of which can be determined from the Borrelia polynucleotide sequences provided herein. Alternatively, utilization of different hybridization and wash conditions allows a general detection system which can detect all Borrelia species.

It would also be desirable to identify primers that permit specific amplification of a target region which does not require the use of a probe for subsequent identification of the target sequence. The efficiency of this process rests upon the knowledge of the primer sequences used to amplify the Borrelia DNA.

Accordingly, one aspect of the invention is a method for determining the presence of a Borrelia polynucleotide in a sample suspected of containing said Borrelia polynucleotide, wherein said Borrelia polynucleotide comprises a selected target region, said method comprising:

(a) amplifying the target region to a detectable level, wherein said target region contains a Borrelia 16S ribosomal polynucleotide sequence;

(b) providing a polynucleotide probe containing a sequence which is complementary to the Borrelia 16S ribosomal polynucleotide sequence in the target region;

(c) incubating the amplified target region with the polynucleotide probe under conditions which allow specificity of hybrid duplexes; and (d) detecting hybrids formed between the amplified target region and the polynucleotide probe.

Another aspect of the invention provides a method for amplifying a target region in a 16S ribosomal Borrelia polynucleotide comprising:

(a) providing a set of primers, wherein a first primer contains a region which is sufficiently complementary to a sequence in a sense strand of 16S ribosomal Borrelia polynucleotide to prime the synthesis of a DNA strand which is a complement to the sense strand of the target region, and a second primer which contains a region which is sufficiently complementary to a sequence in an antisense strand of 16S ribosomal Borrelia polynucleotide to prime the synthesis of a DNA strand which is a complement to the antisense strand of the target region;

(b) providing a sample suspected of containing the target region;

(c) contacting the sample with four different nucleoside triphosphates, the first and second primers, and a primer- and template-dependent polymerizing agent, under conditions whereby the primers are extended using the target region as template, yielding primer extension products;

(d) treating the primer extension products under denaturing conditions to separate the primer extension products from their templates; and (e) repeating steps (c) and (d) until the target sequence is amplified to a level which allows it to be detected above non-target levels in the sample.

Yet another aspect of the invention provides an oligonucleotide probe for detecting or monitoring Borrelia species nucleic acid in a sample comprising a sequence capable of hybridizing to an amplified 16S ribosomal RNA of Borrelia or a sequence complementary thereto.

The invention also contemplates a polymerase chain reaction (PCR) kit for amplifying a target region in a Borrelia 16S ribosomal polynucleotide, comprising:

(a) a first container in which are stored a set of primers, one for each strand of the Borrelia nucleic acid sequence to be amplified, which primers are sufficiently complementary to substantially conserved regions among the Borrelia 16S ribosomal DNA to hybridize therewith, such that an extension product synthesized from each primer is substantially complementary to a strand of the Borrelia DNA sequence being amplified, such that the extension product synthesized from each primer, when separated from its complement, can serve as a template for the synthesis of the extension product of the other primer; and (b) one or more additional containers in which are stored reagents for performing PCR amplification and, optionally, probe hybridization.

DETAILED DESCRIPTION OF THE INVENTION

A. Definitions

As used herein, a "biological sample" refers to a sample of tissue or fluid isolated from an individual, including but not limited to, for example, skin, plasma, serum, spinal fluid, synovial fluid, lymph fluid, urine, blood cells, organs, such as the spleen or the kidney, and also samples of in vitro cell culture constituents.

As used herein, the terms "polynucleotide" and "oligonucleotide" refer to primers, probes, oligomer fragments to be detected, oligomer controls and unlabeled blocking oligomers and shall be generic to polydeoxy-ribonucleotides (containing 2-deoxy-D-ribose), to polyribonucleotides (containing D-ribose), and to any other type of polynucleotide which is an N-glycoside of a purine or pyrimidine base, or modified purine or pyrimidine bases. There is no intended distinction in length between the term "polynucleotide" and "oligonucleotide", and these terms will be used interchangeably. These terms refer only to the primary structure of the molecule. Thus, these terms include double- and single-stranded DNA, as well as double- and single-stranded RNA.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

As used herein, the term "target sequence" refers to a region of the polynucleotide which is to be amplified and/or detected.

The term "probe" refers to a polynucleotide or oligonucleotide which forms a hybrid structure with a sequence in a target region, due to complementarity of at least one sequence in the probe with a sequence in the target region. The probe may contain a sequence complementary to either the sense or antisense strand of the target region. Preferably the probe, however, does not contain a sequence complementary to sequence(s) used to prime the polymerase chain reaction.

As used herein, the term "thermostable nucleotide polymerase" refers to an enzyme which is relatively stable to heat when compared to nucleotide polymerases from *E. coli* and which catalyzes the polymerization of nucleosides. Generally, the enzyme will initiate synthesis at the 3'-end of the target sequence utilizing the primer, and will proceed in the 3'-direction along the template until synthesis terminates. A representative thermostable enzyme isolated from *Thermus acuaticus* (Tag) is described in U.S. Pat. No. 4,889,818 and a method for using it is described in Saiki et al., (1988), *Science* 239:487.

An "individual", as used herein, refers to vertebrates, particularly members of the mammalian species, and includes, but is not limited to, domestic animals, sport animals, wild animals, and primates, including humans; and invertebrates such as ticks.

B. General Method

The practice of the present invention will employ, unless otherwise indicated, conventional techniques of molecular biology, microbiology and recombinant DNA techniques, which are within the skill of the art. Such techniques are explained fully in the literature. See, e.g., Sambrook, Fritsch & Maniatis, *Molecular Cloning; A Laboratory Manual*, Second Edition, (1989) (hereinafter "Maniatis"); *Oligonucleotide Synthesis* (M. J. Gait, ed., 1984); *Nucleic Acid Hybridization* (B. D. Hames & S. J. Higgins, eds., 1984); *A Practical Guide to Molecular Cloning* (B. Perbal, 1984); and a series, *Methods in Enzymology* (Academic Press, Inc.). All patents, patent applications, and publications mentioned herein, both supra and infra, are hereby incorporated by reference.

The various aspects of the invention described herein allows the detection of the etiologic agent of Lyme disease, by virtue of the detection in biological samples of the DNA derived from the bacteria. As used herein, a polynucleotide "derived from" a designated polypeptide sequence refers to a polynucleotide sequence which is comprised of a sequence of approximately at least 6 nucleotides, preferably at least about 10–12 nucleotides, and more preferably at least about 15–20 nucleotides corresponding to a region of the designated nucleotide sequence. "Corresponding" means identical to or complementary to the designated sequence.

The derived polynucleotide is not necessarily physically derived from the Borrelia nucleotide sequence, SEQ ID NO: 1, but may be generated in any manner, including chemical synthesis, DNA replication, reverse transcription or a combination thereof. The term "recombinant polynucleotide" intends a polynucleotide of genomic DNA or RNA, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature; and (3) is not found in nature.

The methods of the present invention enable one to obtain greater sensitivity and accuracy than heretofore possible with prior art detection methods for Borrelia. The basic PCR process is carried out as follows.

A sample is provided which is suspected of containing a particular nucleic acid sequence of interest, the "target sequence". The nucleic acid contained in the sample may be first reverse transcribed into cDNA, if necessary, and then denatured, using any suitable denaturing method, including physical; chemical, or enzymatic means, which are known to those of skill in the art. A preferred physical means for strand separation involves heating the nucleic acid until it is completely (>99%) denatured. Typical heat denaturation involves temperatures ranging from about 80° C. to about 105° C., for times ranging from about 1 to 10 minutes.

The denatured DNA strands are then incubated with the selected oligonucleotide primers under hybridization conditions, conditions which enable the binding of the primers to the single oligonucleotide strands. As known in the art, the primers are selected so that their relative positions along a duplex sequence are such that an extension product synthesized from one primer, when it is separated from its complement, serves as a template for the extension of the other primer to yield a replicate chain of defined length.

The primer must be sufficiently long to prime the synthesis of extension products in the presence of the agent for polymerization. The exact length of the primers will depend on many factors, including temperature, source of the primer and use of the method. For example, depending on the complexity of the target sequence, the oligonucleotide primer typically contains about 15–35 nucleotides, although it may contain more or fewer nucleotides. Short primer molecules generally require cooler temperatures to form sufficiently stable hybrid complexes with the template. The primers must be sufficiently complementary to selectively hybridize with their respective strands.

The primers used herein are selected to be "substantially" complementary to the different strands of each specific sequence to be amplified. The primers need not reflect the exact sequence of the template, but must be sufficiently complementary to selectively hybridize with their respective strands. Non-complementary bases or longer sequences can be interspersed into the primer, provided that the primer retains sufficient complementarity with the sequence of one of the strands to be amplified to hybridize therewith, and to thereby form a duplex structure which can be extended by the polymerizing means. The non-complementary nucleotide sequences of the primers may include restriction enzyme sites. Appending a restriction enzyme site to the end(s) of the target sequence is particularly helpful for subsequent cloning of the target sequence.

It is anticipated that there may be a number of strains or geographic isolates of Borrelia with sequences which deviate from the composite sequence provided in SEQ ID No: 1. Therefore, in order to detect such variant strains it is preferable to construct primers which hybridize to conserved regions of the *Borrelia burgdorferi* 16S rRNA gene sequence. The conserved regions may be determined by comparing the nucleotide sequences of several Borrelia strains or isolates essentially as shown in FIG. 6.

The oligonucleotide primers and probes may be prepared by any suitable method. Methods for preparing oligonucleotides of specific sequence are known in the art, and include, for example, cloning and restriction of appropriate sequences, and direct chemical synthesis. The primers may be labeled, if desired, by incorporating means detectable by spectroscopic, photochemical, biochemical, immunochemical, or chemical means.

Template-dependent extension of the oligonucleotide primer(s) is then catalyzed by a polymerizing agent in the presence of adequate amounts of the four deoxyribonucleoside triphosphates (dATP, dGTP, dCTP, and dTTP) or analogs, in a reaction medium which is comprised of the appropriate salts, metal cations, and pH buffering system. Suitable polymerizing agents are enzymes known to catalyze primer- and template-dependent DNA synthesis. Known DNA polymerases include, for example, *E. coli* DNA polymerase I or its Klenow fragment, $T_4$ DNA polymerase, and Tag DNA polymerase. The reaction conditions for catalyzing DNA synthesis with these DNA polymerases are well known in the art.

The products of the synthesis are duplex molecules consisting of the template strands and the primer extension strands, which include the target sequence. These products, in turn, serve as templates for another round of replication. In the second round of replication, the primer extension strand of the first cycle is annealed with its complementary primer; synthesis yields a "short" product which is bounded on both the 5'- and the 3'-ends by primer sequences or their complements. Repeated cycles of denaturation, primer annealing, and extension result in the exponential accumulation of the target region defined by the primers. Sufficient cycles are run to achieve the desired amount of polynucleotide containing the target region of nucleic acid. The desired amount may vary, and is determined by the function which the product polynucleotide is to serve.

The PCR method can be performed in a number of temporal sequences. For example, it can be performed step-wise, where after each step new reagents are added, or in a fashion where all of the reagents are added simultaneously, or in a partial step-wise fashion, where fresh reagents are added after a given number of steps.

In a preferred method, the PCR reaction is carried out as an automated process which utilizes a thermostable enzyme. In this process the reaction mixture is cycled through a denaturing step, a primer annealing step, and a synthesis step. A DNA thermal cycler specifically adapted for use with a thermostable enzyme may be employed, which utilizes temperature cycling without a liquid-handling system, thereby eliminating the need to add the enzyme at every cycle. This type of machine is commercially available from Perkin-Elmer Cetus Instruments and is described in European Patent publication 236,069 published 9 Sep. 1989.

Nested PCR may be performed by using both external primers and "nested" primers. These nested primers define sequences within the target sequence amplified by the external primers. The external primers are generally used to preferentially amplify a specific target. During a second round of amplification, the PCR conditions are designed such that the internal primers preferentially amplify the target region within the product amplified by the external primers. These experiments usually employ sets of primers that have different melting temperatures (Tm). For example, if the external primers have a higher Tm than the internal primers, the annealing temperature used in the first round of amplification is set higher, generally about 50 to 65° C. In addition, the concentrations of the internal primers are generally in excess over the external primers. A ratio of 50 pmoles:5 pmoles is usually sufficient. As the annealing temperature is lowered to, for example, about 35 to 50° C. for the second round of the amplification, preferential amplification of the fully nested product occurs due in part to the limited concentration of the external primers.

The nested system may also be performed using a hemi-nested primer, that is only a single internal primer is used during the second amplification along with the appropriate "external" primer from the first amplification cycle. If this system in employed, appropriate adjustment of the concentration of the dual purpose external primer must be made.

The advantage of these systems is two-fold: 1) the sensitivity of a system can be increased by allowing amplification of a low copy input target sequence; and 2) the specificity of a system can be increased by eliminating amplification of nonspecific sequences. Only sequences which are defined by both the internal and the external primers will be amplified using nested PCR.

After amplification by PCR, the target polynucleotides may be detected directly by gel analysis provided the target DNA is efficiently. amplified and the primers are highly specific to the target region to be amplified. To assure PCR efficiency, glycerol and other related solvents such as dimethyl sulfoxide, can be used to increase the sensitivity of the PCR at the amplification level and to overcome problems pertaining to the sequencing of regions of DNA having strong secondary structure. These problems may include: (1) low efficiency of the PCR, due to a high frequency of templates that are not fully extended by the polymerizing agent or (2) incomplete denaturation of the duplex DNA at high temperature, due to high GC content. The use of such solvents increases the sensitivity of the assay at the level of amplification to approximately several femtograms of DNA (which is believed to correspond to a single spirochete cell). This level of sensitivity eliminates the need to detect amplified target DNA using a probe, and thereby dispenses with the requirements for radioactive probes, gel electrophoresis, Southern blotting, filter hybridization, washing and autoradiography. The concentration range for glycerol is about 5%–20% (v/v), with 10% being preferred, and the DMSO concentration range is about 3%–10% (v/v).

Alternatively, the target polynucleotides may be detected by hybridization with a probe polynucleotide which forms a stable hybrid with that of the target sequence under stringent to low stringency hybridization and wash conditions. If it is expected that the probes will be completely complementary (i.e., about 99% or greater) to the target sequence, stringent conditions will be used. If some mismatching is expected, for example if variant strains are expected with the result that the probe will not be completely complementary, the stringency of hybridization may be lessened. However, conditions are chosen which rule out nonspecific/adventitious binding. Conditions which affect hybridization and which select against nonspecific binding are known in the art and are described in, for example, Maniatis et al. (1989). Generally, lower salt concentration and higher temperature increase the stringency of binding. For example, it is usually considered that stringent conditions are incubation in solutions which contain approximately 0.1×SSC, 0.1% SDS, at about 65° C. incubation/wash temperature, and moderately stringent conditions are incubation in solutions which contain approximately 1–2×SSC, 0.1% SDS and about 50°–65° C. incubation/wash temperature. Low stringency conditions are 2×SSC and about 30°–50° C.

Probes for Borrelia target sequences may be derived from either strand of the 16S rRNA DNA sequences described infra, or from new Borrelia isolates. The Borrelia probes may be of any suitable length which span the target region, but which exclude the primers, and which allow specific hybridization to the target region. If there is to be complete complementarity, i.e., if the strain contains a sequence identical to that of the probe, since the duplex will be relatively stable under even stringent conditions, the probes may be short, i.e., in the range of about 10–30 base pairs. If some degree of mismatch is expected with the probe, i.e., if it is suspected that the probe will hybridize to a variant region, the probe may be of greater length, since length seem to counterbalance some of the effect of the mismatch(es).

In certain embodiments of the invention probes have been designed to permit the detection of specific species of Borrelia. With reference to FIG. 2, the probe (SEQ ID No: 31) 5'-CCCGNAAGGGAGGAAGGTATN-3' wherein N at position 5 can be T or C and N at position 21 can be T, C or zero, or the sequence complementary thereto, can distinguish B. burgdorferi species over other Borrelia species using stringent hybridization and wash conditions when N at position 5 is T and N at position 21 is absent. B. hermsii, on the other hand, may be detected when N at position 5 is C and N at position 21 is either C or absent. Once the sequence of the 16S ribosomal gene of the particular species or strain to be detected is determined using the method of the present invention, one of ordinary skill in the art can design the appropriate probes to detect the particular target of interest.

If desired, the probe may also be labeled. A variety of labels which would be appropriate, as well as methods for their inclusion in the probe are known in the art, and include, for example, 32-radioactive atoms, such as $^{32}P$, or other recognizable functionalities, e.g., biotin (preferably using a spacer arm), fluorescent dyes, electron-dense reagents, enzymes capable of forming easily detectable reaction products (e.g., alkaline phosphatase, and horseradish peroxidase), or antigens for which specific antisera or monoclonal antibodies are available.

In order to determine variant Borrelia species or isolates, and thereby to design probes for those variants, the above-described PCR method is utilized to amplify variant regions of the Borrelia 16S rRNA gene, so that the nucleotide sequences of these variant target regions can be determined. Generally, variant types of Borrelia are known to occur in different geographic locations, for example, Europe and North America, including Mid-America, New England, North Central, Southeast, Southwest, Mountain and Pacific regions; or in different vertebrate species which are infected with the spirochete.

In order to amplify the variant target region, primers are designed to flank the suspect region, and preferably are complementary to substantially conserved regions of at least 12 nucleotides long in the 16S rRNA gene. The probe is designed for the variant region with some degree of mismatch expected. Analysis of the nucleotide sequence of the target region may be by direct analysis of the PCR amplified products as described in Gyllensten and Erlich, (1988) Proc Natl Acad Sci USA 85:7652 and in PCT publication WO90/03444, published Apr. 5, 1990.

It may be desirable to determine the length of the PCR product detected by the probe. This may be particularly true if it is suspected that variant Borrelia strains may contain deletions within the target region, or if one wishes to confirm the length of the PCR product. In such circumstances, it is preferable to subject the products to size analysis as well as hybridization with the probe. Methods for determining the size of nucleic acids are known in the art, and include, for example, gel electrophoresis, sedimentation in gradients, and gel exclusion chromatography.

The presence of the target sequence in a biological sample is detected by determining whether a hybrid has been formed between the Borrelia probe and the nucleic acid subjected to the PCR amplification techniques. Methods to detect hybrids formed between a probe and a nucleic acid sequence are known in the art. For example, an unlabeled sample may be transferred to a solid matrix to which it binds, and the bound sample subjected to conditions which allow specific hybridization with a labeled probe; the solid matrix is then examined for the presence of the labeled probe. Alternatively, if the sample is labeled, an unlabeled probe is bound to the matrix, and after exposure to the appropriate hybridization conditions, the matrix is examined for the presence of a label. PCT publication WO89/11548, published Nov. 30, 1989 and Saiki et al., (1988) Proc Natl Acad Sci, USA 86:6230 describe methods of immobilizing multiple probes on a solid support and using hybridization to detect the amplified target polynucleotides of interest. In another alternative procedure, a solution phase sandwich assay may be used with labeled polynucleotide probes, and the methods for the preparation of such probes are described in U.S. Pat. No. 4,820,630, issued Apr. 11, 1989.

C. PCR Kit and Reagents

Also within the scope of the present invention is a PCR kit for use in carrying out any of the aforementioned PCR processes. The diagnostic kits include the probe polynucleotide(s) and the primers in separate containers. Either of these may or may not be labeled. If unlabeled, the ingredients for labeling may also be included in the kit. The kit may also contain other suitably packaged reagents and material needed for the particular hybridization protocol, for example, standards, and/or polymerizing agents, as will as instructions for conducting the test.

In use, the components of the PCR kit, when applied to a nucleic acid sample, create a reagent mixture which enables the detection and amplification of the target nucleic acid sequence. The reagent mixture thus includes the components of the kit as well as a nucleic acid sample which contains the polynucleotide chain of interest.

The following examples are intended to be illustrative of the various methods and compounds of the invention.

EXAMPLES

Example 1

DNA Isolation

Borrelia. cultures were maintained in BSK II medium (Barbour (1984) *Yale J Biol Med* 57:71) at 37° C. and passaged twice a week. The species and strains propagated for this study included *B. burgdorferi* from *I. dammini* (ATCC 35210), *B. burgdorferi* from *I. ricinus* (ATCC 35211), and *B. hermsii* from *O. hermsii* (ATCC 35209).

Total genomic Borrelia DNA was prepared as follows. Briefly, spirochetes were pelleted from 100 ml of a stationary-phase culture and resuspended in 0.5 ml total volume of 446 ul of TE (stock solution=1 mM Tris-HCl, 0.01 mM EDTA, pH 8.0), 5 ul of 10 mM DTT, 20 ul of 10 mM EDTA, 25 ul of 0.5% SDS and 3.8 ul of Proteinase K (150 ug/ml). The sample was incubated at 37° C. for 1 hr. The sample was subsequently extracted twice with phenol-chloroform (1:1) and the upper layer re-extracted. The organic lower layer was also extracted twice with phenol-chloroform and added to the aqueous layer from above. Nucleic acid was precipitated by adjusting the salt concentration of 0.3M sodium acetate and by the addition of 0.6 volumes of isopropanol. The precipitated DNA was pelleted from the solution, washed once with 0.5 ml of 70% ethanol, and resuspended in 50 ul of TE (stock solution) overnight at 4° C. to solubilize the DNA. This sample was then digested with RNase A (100 ug/ml) at 37° C. for 1 hr and then extracted twice with phenol/chloroform, precipitated, and resuspended in 25 ul of TE as described above. DNA concentration was determined by optical density.

Example 2

PCR Amplification of 16S Ribosomal DNA

Oligonucleotide primers, based upon bacterial 16S rDNA sequence information, were prepared by either the phosphotriester method as described by Duckworth et al., (1981) *Nuc Acids Res* 9:1691 or by the phosphoramidite method as described by Beaucage and Caruthers, (1981) *Tet Letts J Am Chem Soc* 22:1859, and Matteucci and Caruthers, (1981) *J Am Chem Soc* 103:3185, and were prepared using commercially available automated oligonucleotide synthesizers, such as the Applied Biosystems 380A DNA synthesizer. The upstream and downstream primers used to amplify and partially sequence the *B. burgdorferi* 16S ribosomal RNA gene are listed below, along with the corresponding nucleotide position according to the numbering of the *E. coli* 16S ribosomal RNA gene sequence:

PL3 (5'-ACAAGCGGTGGAGCATGTGG-3') 934→953 (SEQ ID No: 25)

PL6 (5'-GGTTAAGTCCCGCAACGAGCGC-3') 1087→1108 (SEQ ID No: 26)

DG73 (5'-TACGTTCCCGGGCCTTGTAC-3') 1375→1394 (SEQ ID No: 27)

DG74 (5'-AGGAGGTGATCCAACCGACA-3') 1522→1540 (SEQ ID No: 28) The arrow position designates the direction of synthesis.

Asymmetric PCR was performed according to the procedure of Gyllensten ("Direct Sequencing of In Vitro Amplified DNA" in *PCR Technology*, Principles and Applications for DNA Amplification, ed. Erlich, Stockton Press 1989) in which the molar ratios of the primers utilize first one primer in excess concentration (50 pmoles of DG73 - SEQ ID No: 27) with the other primer in limiting concentration (1 pmole of DG74 - SEQ ID No: 28) in a 100 ul PCR. The reaction is also performed with the molar ratios of the primers reversed. In general, a ratio of 50 pmol:0.5 pmol for a 100 ul PCR reaction will result in about 1–3 pmol of single-stranded DNA (ssDNA) after 30 cycles of PCR. The recommendation in Gyllensten to reduce the concentration of each dNTP for asymmetric PCR was followed. Approximately 62.5 uM of each dNTP was used for a 100 ul PCR reaction buffer.

The ssDNA generated was purified for sequencing using Amicon-Centricon 30 concentrator tubes. The purified DNA was then sequenced using an alpha-[$^{35}$S]thio dATP, limiting primer and applying conventional protocols for sequencing using Tag DNA polymerase (see, for example, "Sequencing with Tag DNA Polymerase" in *PCR Protocols*, A Guide to Methods and Applications, ed. Innis et al., Academic Press, Inc. 1990). The products were resolved on buffer gradient sequencing gels.

From this reaction, approximately 84 nucleotides of Borrelia DNA were sequenced, corresponding to nucleotides 1409 to 1493, designated in FIG. 1. In separate PCR reactions, two different upstream primers (PL3 - SEQ ID No: 25 and PL6 - SEQ ID No: 26) designed to overlap the same region of the target DNA from the same organism, were used to verify the sequence previously obtained. The homology for the region sequenced was 100%.

The *B. burgdorferi* sequence obtained from this experiment was aligned for maximum identity with nucleotides 661 through 1542 of the *E. coli* 16S rRNA gene sequence SEQ ID No:13). As depicted in this figure, the numbering of the Borrelia sequences (designated as aligning with the *E. coli* 16S rRNA gene) includes deleted, additional and substituted bases as would be clear to one of skill in the art. The asterisks mark bases heterogeneous between the two genera. Bases designated as "N" could not be determined from the sequencing gel. However, if it is desired to design a primer or internal probe which is to be aligned in the region containing any "N," thymine would be a preferred substitute, unless this region contains a base which is conserved among bacterial 16S rRNA genes.

This sequence information was used to design new primers which amplified Borrelia species but not other common pathogens, e.g., *E. coli, S. aureus* and *P. aeruginosa*. The new primers include those designated below and their positions, numbered in accordance with the *E. coli* 16S ribosomal RNA gene sequence as shown in FIG. 2.

DD02 (3'-CCCTCACTAAACATACCT-5') (SEQ ID No: 2)

DD03 (5'-CACCCGAGTTGAGGATACC-3') (SEQ ID No: 3)

DD05 (5'-ATAGTTAGAGATAATTATTC-3') (SEQ ID No: 5)

DD06 (5'-ATCTGTTACCAGCATGTAAT-3') (SEQ ID No: 6)

DD07 (5'-CGTGCTACAATGGCCTG-3') (SEQ ID No: 7)

DD08 (5'-GGAAGATAGTTAGAGATAATTATTC-3') (SEQ ID No: 8)

DD09 (5'-CTTGTTATCTGTTACCAGCATGTAAT-3') (SEQ ID No: 9)

DD10 (5'-TATCTGTTACCAGCATGTAAT-3') (SEQ ID No: 10)

DD11 (5'-ACACACGTGCTACAA-3') (SEQ ID No: 11)

DD12 (5'-CAGATAAGACTGCCGGTGATAAGTC-3')
(SEQ ID No: 12)

Primers DD02 (SEQ ID No: 2) and DD03 (SEQ ID No: 3) were used to amplify Borrelia DNA in a 3-step cycling PCR reaction. To 100 ul of the PCR buffer, including 62.5 um of each dNTP, 5 units/100 ul of Taq DNA polymerase, 2.4 mM $MgCl_2$, were added equimolar concentrations (50 pmoles) of primers DDO2 (SEQ ID No: 2) and DD03 (SEQ ID No: 3) to approximately $1.7 \times 10^7$ fg of the target DNA. Each resulting solution was heated first to 95° C. for 5 min followed by 25 cycles of a denaturing step at 95° C. for 25 sec, an annealing step at 50° C. for 25 sec and an extension step at 72° C. for 2 min. A final extension step was performed at 72° C. for 10 min.

Purified DNAs from 25 species of medically significant bacteria including 16 spirochetes from the Treponema and Leptospira genera were amplified by the PCR assay as taught above. Since the results indicated that these conditions were not completely specific for Borrelia, a second cycling format was tested. The PCR cycling was increased to 35 cycles and the annealing temperature was raised to 60°C. for 25 sec. As shown in Table 1, amplification under these conditions was observed only for *B. burgdorferi, B. hermsii* and *T. pectinovorum*.

In addition to modifying the annealing temperature, a third format was developed to reduce the overall assay performance time. In this format, a two-step cycling reaction wherein the denaturing step is performed at 95° C. for 25 sec and the annealing step is performed at 60° C. for 25 sec, for 30 cycles, was tested. This 2-step PCR format proved to provide a similar level of specificity as that observed in the second format, 3-step cycling reaction, and was therefore adopted for all subsequent PCR assays.

TABLE 1

Summary of Lyme Disease Specificity Results

| Organism | Strain ATCC/Other | Primers DD02/DD03 | Probe DD04 | Source |
|---|---|---|---|---|
| BORRELIA SP. | | | | |
| burgdorferi | 35211 | + | + | |
| burgdorferi | 35210 | + | + | |
| burgdorferi | Y297[a] | + | + | |
| burgdorferi | YN40[a] | + | + | |
| burgdorferi | CA4-3[b] | + | + | |
| burgdorferi | CA7-7[b] | + | + | |
| hermsii | 35209 | + | – | |
| TREPONEMA SP. | | | | |
| denticola | 33520 | – | – | Subgingival plaque |
| denticola | 35404 | – | – | Human periodontal pocket |
| pallidum | 27087 | – | – | Human syphilis |
| pectinovorum | 33768 | – | – | Subgingiva |
| socranskii sep. buccale | 35534 | – | – | Subgingival plaque of patient with periodontitis |
| socranskii sep. paredis | 35535 | – | – | Subgingival plaque of patient with periodontitis |
| socranskii sep. socranskii | 35536 | – | – | Subgingival plaque of patient with periodontitis |
| vincentii | 35580 | – | – | Patient with periodontitis |

TABLE 1-continued

Summary of Lyme Disease Specificity Results

| Organism | Strain ATCC/Other | Primers DD02/DD03 | Probe DD04 | Source |
|---|---|---|---|---|
| LEPTOSPIRA SP. | | | | |
| inadi sv. lyme | 43289 | – | – | Human skin |
| interrogans st. autumnalis | 23476 | – | – | Human |
| interrogans st. budapest | 23581 | – | – | Human |
| interrogans st. icterohaemorrhagiae | 43642 | – | – | Human blood |
| weilii sv. celledoni | 43285 | – | – | Human blood |
| ADDITIONAL BACTERIA | | | | |
| N. gonorrhoeae | | – | – | |
| S. typhi | | – | – | |
| E. coli | | – | – | |
| P. aeruginosa | | – | – | |
| S. aureus | | – | – | |
| K. pneumoniae | | – | – | |
| S. marcescens | | – | – | |
| E. aerogenes | | – | – | |
| S. pneumoniae | | – | – | |

[a]= Strains provided by David Persing at Yale University
[b]= Strains provided by Robert Lane at the University of California at Berkeley [Lane et al., (1989) J Clin Microbiol 27:2344]

The same group of organisms listed in Table 1 and additional strains of *B. burgdorferi* and other Borrelia species were also tested in the 2-step PCR format to test for the specificity of primers DD02 (SEQ ID No: 2) and DD06 (SEQ ID No: 6) for Borrelia DNA. One modification to the 2-step format employed a decrease in the anneal temperature to 55° C. from 60° C. The results of this experiment were generally 100% specific for *B. burgdorferi* as none of the other spirochetes or eubacteria were amplified except for *L. interrogans* st. *icterohaemorrhagiae*. However, the amplification system is species specific when used in conjunction with probe hybridization.

TABLE 2

Additional Strains Tested

| Organism | Strain ATCC/Other | Primers DD02/DD03 | Probe DD04 | Source |
|---|---|---|---|---|
| BORRELIA SP. | | | | |
| burgdorferi | 35211 | + | + | |
| burgdorferi | 35210 | + | + | |
| burgdorferi | Y297[a] | + | + | |
| burgdorferi | YN40[a] | + | + | |
| burgdorferi | CA4-3[b] | + | + | |
| burgdorferi | CA7-7[b] | + | + | |
| burgdorferi | MEN ZN-6-88 | + | + | I. pacificus |
| burgdorferi | HUM 78-1-4 | + | + | I. pacificus |
| burgdorferi | LAKE 3-3-9 | + | + | I. pacificus |
| burgdorferi | SC 5-2-89 | + | + | I. pacificus |
| burgdorferi | BUCO 2-10-89 | + | + | I. pacificus |
| burgdorferi | SON 3-3-5 | + | + | I. pacificus |
| burgdorferi | CONN 2591 | + | + | I. pacificus |
| burgdorferi | NEV 3-2-88 | + | + | I. pacificus |
| burgdorferi | SON 1-88 | + | + | I. pacificus |

TABLE 2-continued

Additional Strains Tested

| Organism | Strain ATCC/Other | Primers DD02/DD03 | Probe DD04 | Source |
|---|---|---|---|---|
| burgdorferi | DN 1-2-7 | + | + | I. pacificus |
| burgdorferi | FRE 501-3-5 | + | + | I. pacificus |
| burgdorferi | TRI 5-2-89 | + | + | I. pacificus |
| burgdorferi | WISC 21644 | + | + | I. pacificus |
| burgdorferi | TUO 1-3-89 | + | + | I. pacificus |
| burgdorferi | Millbrook 25015 | + | + | I. pacificus |
| burgdorferi | 53899 | + | + | Human CSF |
| BORRELIA SP. | | | | |
| hermsii | 35209 | + | – | |
| hermsii | Conrad | + | – | |
| hermsii | HSI | + | – | |
| hermsii | York | + | – | |
| hermsii | 4229 | + | – | |
| coriaceae | | + | – | |
| parkeri | | + | – | |
| turicatae | | + | – | |
| anserina | | + | – | |
| TREPONEMA SP. | | | | |
| denticola | 33520 | – | – | Subgingival plaque |
| denticola | 35404 | – | – | Human periodontal pocket |
| pallidum | 27087 | – | – | Human syphilis |
| pectinovorum | 33768 | – | – | Subgingiva |
| socranskii sep. buccale | 35534 | – | – | Subgingival plaque of patient with periodontitis |
| socranskii sep. paredis | 35535 | – | – | Subgingival plaque of patient with periodontitis |
| socranskii sep. socranskii | 35536 | – | – | Subgingival plaque of patient with periodontitis |
| vincentii | 35580 | – | – | Patient with periodontitis |
| LEPTOSPIRA SP. | | | | |
| inadi sv. lyme | 43289 | – | – | Human skin |
| interrogans st. autumnalis | 23476 | – | – | Human |
| interrogans st. budapest | 23581 | – | – | Human |
| interrogans st. icterohaemorrhagiae | 43642 | + | – | Human blood |
| weilii sv. ceiledoni | 43285 | – | – | Human blood |
| ADDITIONAL BACTERIA | | | | |
| N. gonorrhoeae | | – | – | |
| S. typhi | | – | – | |
| E. coli | | – | – | |
| P. aeruginosa | | – | – | |
| S. aureus | | – | – | |
| K. pneumoniae | | – | – | |
| S. marcescens | | – | – | |
| E. aerogenes | | – | – | |
| S. pneumoniae | | – | – | | a and b - See Table 1.

Example 3
Specificity of PCR Assay

Specific detection of *B. burgdorferi* was accomplished using hybridization of a radioactively labeled oligonucleotide probe to amplified DNA analyzed by agarose gel electrophoresis and Southern transfer.

The probe DD04 (CCCGTAAGGGAGGAAGGTAT) (SEQ ID No: 4) was labeled with $^{32}$P-ATP and T$_4$ polynucleotide kinase following standard procedures. The unincorporated nucleotides were separated from the incorporated label using a NucTrap™ push column (Stratagene) according to the manufacturer's instructions.

About 5 ul of each amplified PCR product were resolved on a 2% NuSieve/0.5% Seakem agarose gel and visualized by ethidium bromide fluorescence. Hybridization conditions for Southern analysis employed 5x SSPE, 5x Denhardt's solution and 0.1% SDS. The membrane was prehybridized in the buffer for 2 hrs at 60° C. prior to the addition of about 70 ul of the DD04 labeled probe. Filters were hybridized at 60° C. overnight and then washed in 5x SSPE, 0.1% SDS at room temperature for 10 min, followed by 2 washes in 2x SSPE, 0.1% SDS at 60° C. for 15 min and a last wash step in 2x SSPE, 0.1% SDS at 60° C. for 30 min. These stringent conditions were effective to eliminate any signal from *B. hermsii*.

As shown in Tables 1 and 2, the use of the internal probe DD04 (SEQ ID No: 4) offers an assay that is 100% sensitive and specific for *B. burgdorferi*.

Example 4

Species Specificity Using Primers DD06 and DD02

Amplification of the *B. burgdorferi* target DNA was tested in a PCR with primers DD02 (SEQ ID No: 2) and DD06 (SEQ ID No: 6) in the presence of glycerol and increasing cycling conditions to monitor the sensitivity of the reaction. A 100 ul PCR assay was run using purified *B. burgdorferi* DNA in varying concentrations ($1.7 \times 10^0$ through $1.7 \times 10^3$ fg); 50 pmol of each primer; 1.5 mM MgCl$_2$; 62.5 uM of each dNTP/100 ul reaction; 5 units of Taq DNA polymerase/100 ul reaction; and 0 to 15% glycerol (v/v).

The resulting solutions were heated first to 95° C. for 5 min, followed by 30 to 55 cycles of PCR (increasing at five cycle increments) using the following temperature profile:

Denaturation 95° C., 25 sec

Annealing 55° C., 25 sec

A final extension step was performed at 72° C. for 10 min. The products of these reactions were separated by electrophoresis using a 2% NuSieve/0.5% Seakem agarose gel, stained with ethidium bromide and visualized by UV light. A photograph of this gel is shown in FIG. 3.

Figure 3A:
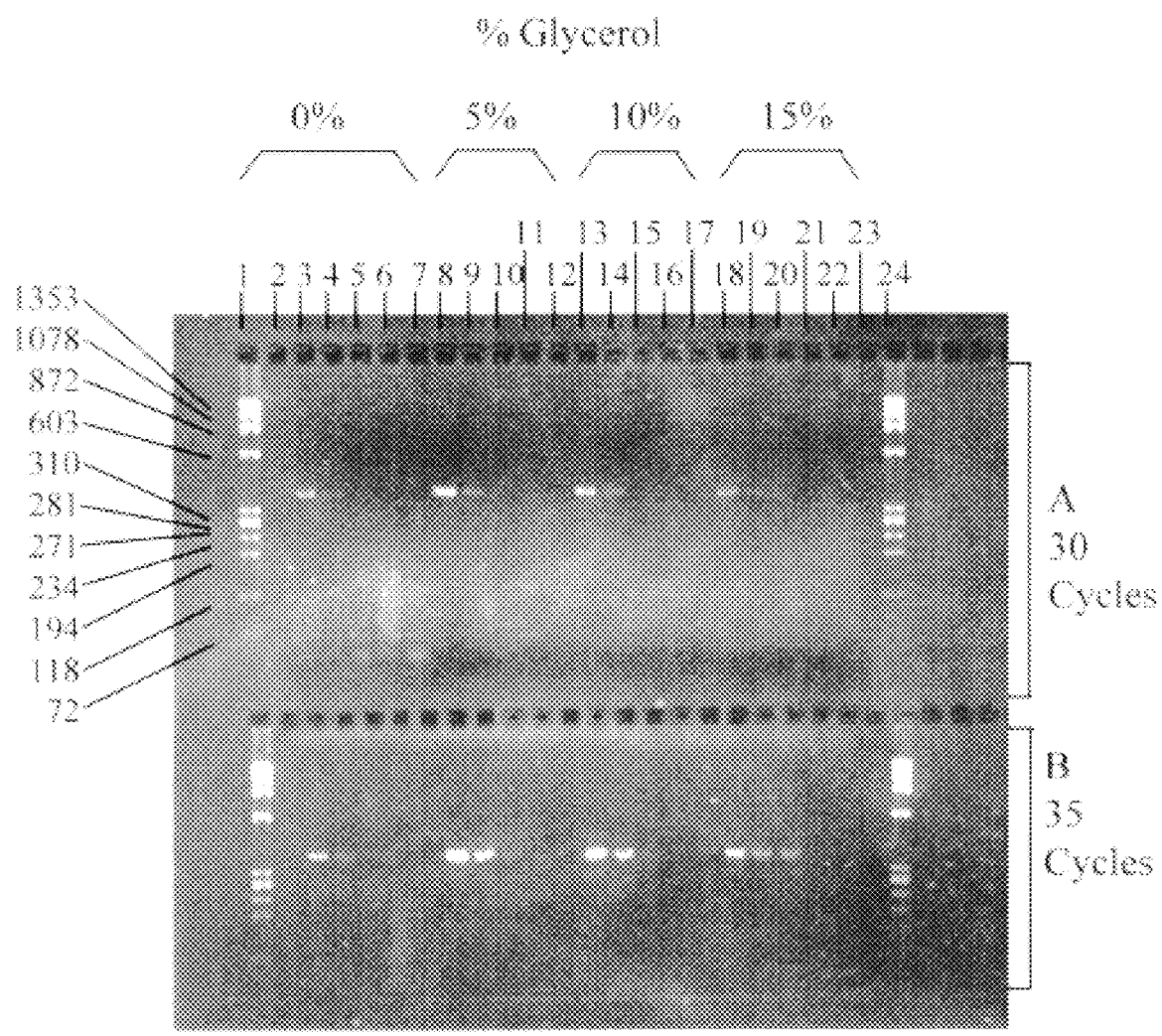
FIG. 3, part a illustrates a photograph of a 2% NuSieve plus 0.5% Seakem agarose gel visualized using ethidium bromide and UV light. This photograph demonstrates amplification of approximately 1.7 femtograms (fg) of *B. burgdorferi* DNA using the primers DD02 (SEQ ID No: 2) and DD06 (SEQ ID No: 6) FIG. 3, parts B, C, D, E, and F illustrate photographs which further demonstrate amplification of *B. burgdorferi* DNA.

FIG. 3 provides 3 different gels, each gel representing two different cycling conditions. FIG. 3A was run for 30 cycles, FIG. 3B for 35 cycles, FIG. 3C for 40 cycles, FIG. 3D for 45 cycles, FIG. 3E for 50 cycles and FIG. 3F for 55 cycles. The samples loaded onto Lanes 1 through 24 remained the same throughout the three experiments, varying only by the number of PCR cycles performed and the amount of glycerol present (designated in FIG. 3). Lanes 1 and 24 are molecular weight markers of X174 cut with HaeIII (New England Biolabs); Lanes 2 and 23 are blank; Lanes 3, 8, 13 and 18 contain $1.7 \times 10^3$ fg/100 ul of *B. burgdorferi* DNA; Lanes 4, 9, 14 and 19 contain $1.7 \times 10^2$ fg/100 ul of *B. burgdorferi* DNA; Lanes 5, 10, 15 and 20 contain $1.7 \times 10^1$ fg/100 ul of *B. burgdorferi* DNA; Lanes 6, 11, 16 and 21 contain $1.7 \times 10$ hu 0 fg/100 ul of *B. burgdorferi* DNA; and Lanes 7, 12, 17 and 22 are negative controls containing 50 ul H$_2$O and 50 ul of the PCR cocktail.

The results show that the presence of glycerol increased the sensitivity of the PCR by one hundred-fold. By forty cycles (FIG. 3C, Lane 11) the sensitivity is at the one bacterium level (1.7 fg), and is very noticeable by 45 cycles (FIG. 3D, Lanes 11, 16 and 21). At 50 and 55 cycles the band at the one bacterium level is prominent at all concentrations of glycerol. In the absence of glycerol amplification can be seen at $1.7 \times 10^2$ fg (FIGS. 3A, B, C, Lane 4). As the cycle number increases the samples without glycerol deteriorate into smears. The addition of glycerol appears to maintain the integrity of the PCR reaction at high cycle numbers.

Example 5

Probe Experiments

The following experiment was designed to test whether the sensitivity of the PCR assay could be increased by detecting the amplified Borrelia target sequence with a gene probe.

detect target DNA amplified after 40 and 55 cycles in the absence of glycerol at the $1.7 \times 10^2$ fg level, a 100-fold decrease in sensitivity.

The following probes, derived from the region including nucleotides 1443 to 1474 of FIG. 1 have been designed to test the specificity of detection among several species of Borrelia. Each of these probes detected all Borrelia species under low stringency hybridization and wash conditions. At minimum, a probe comprising, for example, the core sequence 5'-CCGNAAGGGAGG-3'(SEQ. ID NO: 32) wherein N is T or C is useful for detection of Borrelia species.

| SENSE (5'–3') | | |
|---|---|---|
| DD04 | CCCGTAAGGGAGGAAGGTAT | (SEQ ID No: 4) |
| DD15 | TAACCCGTAAGGGAGGA | (SEQ ID No: 15) |
| DD21 | AACCCGTAAGGGAGGAAGGTATTTAAG | (SEQ ID No: 21) |
| DD23 | TTCTAACCCGTAAGGGAGGA | (SEQ ID No: 23) |
| B. hermsii | CCCGCAAGGGAGGAAGGTATC | (SEQ ID No: 33) |
| ANTISENSE (5'–3') | | |
| DD14 | ATACCTTCCTCCCTTACGGG | (SEQ ID No: 14) |
| DD16 | TCCTCCCTTACGGGTTA | (SEQ ID No: 16) |
| DD22 | CTTAAATACCTTCCTCCCTTACGGGTT | (SEQ ID No: 22) |
| DD24 | TCCTCCCTTACGGGTTAGAA | (SEQ ID No: 24) |
| B. hermsii | ATATACCTTCCTCCCTTTCGGG | (SEQ ID No: 34) |

About 15 ul of the PCR product was denatured by incubation with 15 ul of a denaturant (0.8M NaOH, 50 mM EDTA) for 3 min at room temperature. About 20 ul of the denatured PCR product (using either a 40 or 55 cycle reaction run in the presence or absence of 10% glycerol—see Example 4) was spotted onto a 0.45 micron nylon membrane (Genetrans; Plasco, Inc.), and fixed onto the membrane by UV irradiation.

The amplified DNA immobilized on the nylon membrane was prehybridized with a hybridization solution containing 5 ml of 20x SSPE, pH 7.4, 0.2 ml of 10% SDS, 1 ml of Denhardt's solution and 13.8 ml of $H_2O$ for 1 hr at 50° C.

About 70 ul of the kinased probe DDO4 (SEQ ID No: 4) (see Example 3) were added to the membrane in solution and hybridization was run for 3–5 hrs at 50° C. The membrane was then washed in 5x SSPE, 0.1% SDS at room temperature for 10 min, then at 50° C. for 10 min, followed by a wash in 2x SSPE, 0.1% SDS at 50° C. for 10 min. To detect $^{32}$P-labeled DNAs, the blots were covered with Saran Wrap and exposed to X-ray film at –70° C. for 4 hrs.

Figure 4:
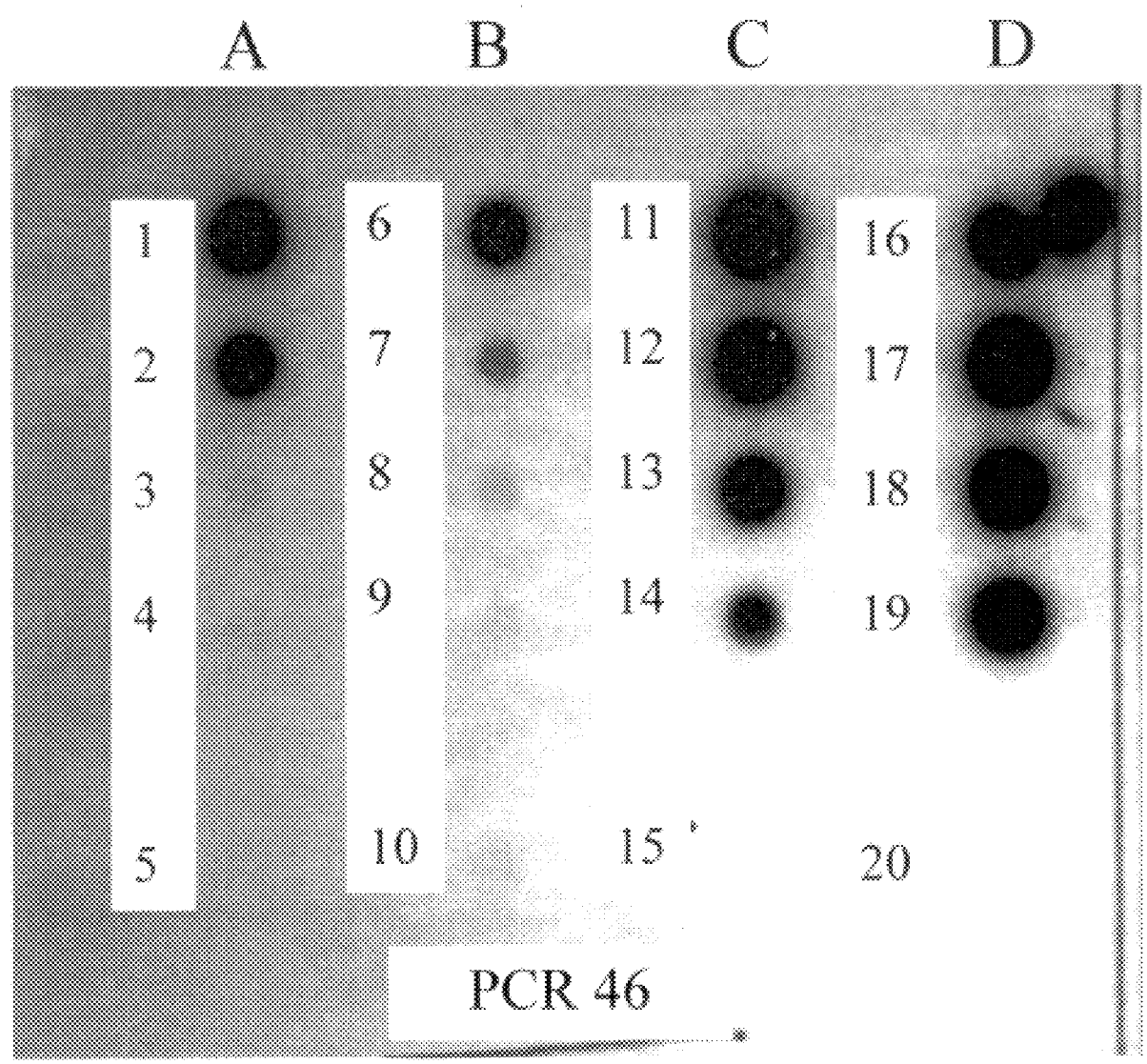
FIG. 4 is an example of the sensitivity of detection of *B. Burgdorferi* DNA showing dot blot analysis of the PCR-amplified samples using the DD04 (SEQ ID No: 4) radio-labeled probe.

The results are shown in the autoradiograph illustrated in FIG. 4. Columns A and B represent 40 and 55 cycles, respectively, of B. burgdorferi DNA amplified in the absence of glycerol and Columns C and D represent 40 and 55 cycles, respectively, of B. burgdorferi DNA amplified in the presence of 10% glycerol. The various amounts of B. burgdorferi DNA present in each blot are presented in the figure in descending order ($1.7 \times 10^3$ fg, $1.7 \times 10^2$ fg, $1.7 \times 10^1$ fg, and $1.7 \times 10^0$ fg), in each column along with appropriate negative controls (bottom line). The results indicate that amplification of the gene sequence by PCR employing glycerol, coupled with the gene probe, allows one to detect the target in 1.7 fg of total DNA in either the 40- or 55-cycled amplified product. In contrast, the probe can only In addition, given the information provided in FIG. 6 regarding the B. hermsii 16S rRNA gene sequence, probes specific for the detection of this Borrelia species may be designed. Such probes include, for example, sequences which incorporate specific base substitutions between B. burgdorferi and B. hermsii. Illustrative probes include:

DD25 (5'3') AAAGCGACAGAACAGTGA (SEQ ID No: 29) and the complementary sequence thereto DD27 (5'3') GGACTCAGATAAGACTGC (SEQ ID No: 30) and the complementary sequence thereto Example 6

Nested Systems

The nested primer system may be performed in a single tube eliminating the carry over contamination which can be a problem with conventional nested systems. In the single tube coamplification. PCR, the external primers DD17 3'-GTCACCTGCCTCACTAAACATACCT-5'(SEQ ID No: 17) and DD18 5'-GTCCAGCATCTGTTACCAGCATGTAAT-3'(SEQ ID No: 18) have melting temperatures of 66° C. and 70° C., respectively, and the internal primers DD19 3'-ATACCTTCCTCCCTTA-5'(SEQ ID No: 19) and DD20 5'-GTGCTACAATGGCCT-3'(SEQ ID No: 20) have melting temperatures of 48° C. and 52° C., respectively.

A "Mastermix" composed of 20 ul 50% glycerol (10% total), 12.5 ul glass distilled $H_2O$, 10.0 ul 10x buffer (GeneAmp), 2.5 ul each DNTP (250 uM total), 1 ul DD17 (SEQ ID No: 17) (5 uM), 1 ul DD18 (SEQ ID No: 18) (5 uM), 1 ul DD19 (SEQ ID No: 19) (50 uM), 1 ul DD20 (SEQ ID No: 20) (50 uM) and 1 ul Taq polymerase (5 units/100 ul reaction) were added to a 50 ul sample of human urine (prepared as described in Example 11).

The solution was heated first to 95° C. for 5 minutes followed by 25 cycles of a denaturing step at 95° C. for 45 seconds and an annealing step at 60° C. for 45 seconds. For the next 25 cycles, the denaturing step was performed at 95° C. for 45 seconds and an annealing step at 45° C. for 45 seconds. A final extension step was performed at 72° C. for 10 minutes, followed by a 10° C. soak in the thermocycler overnight.

As controls, 50 ul of sample were added to a 50 ul volume of the Mastermix containing either the set of external or internal primers. In the PCR using the external primers DD17 (SEQ ID No: 17) and DD18 (SEQ ID No: 18), the cycling conditions were identical except that the entire 50 cycles were run using an anneal temperature of 60° C. Similarly, in the PCR using the internal primers DD19 (SEQ ID No: 19)and DD20 (SEQ ID No: 20), the entire 50 cycles were run using an anneal temperature of 45° C.

Figure 5:
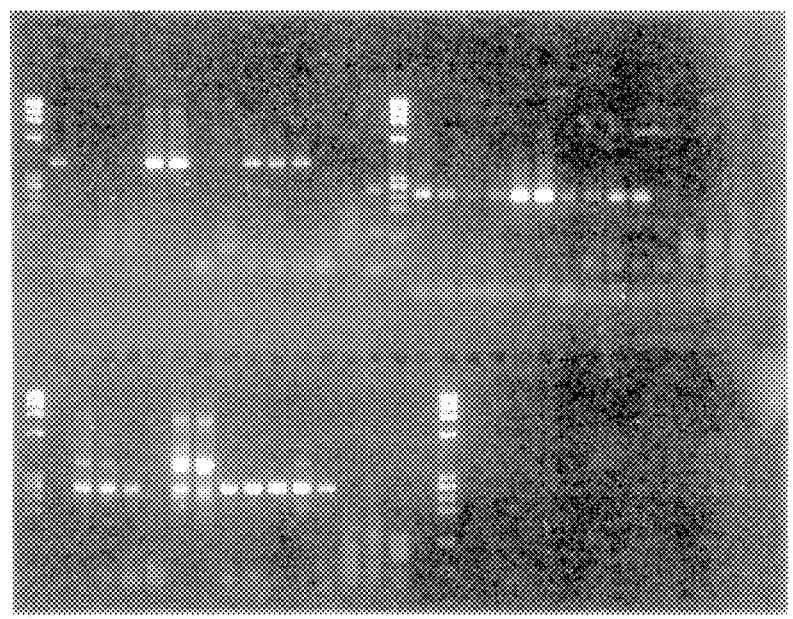
FIG. 5 is an photograph of an agarose gel illustrating the results of a nested PCR coamplification experiment using external primers DD17 (SEQ ID No: 17) and DD18 (SEQ ID No: 18) and internal primers DD19 (SEQ ID No: 19) and DD20 (SEQ ID No: 20).

FIG. 5 provides the results of both the control primer amplification products and the coamplification products using both sets of primers. The legend to the lane samples is as follows:

| Lane No. | DNA/Control | Concentration |
| --- | --- | --- |
| 2, 17, 33 | B. burgdorferi 210 | 2000 fg |
| 3, 18, 34 | B. burgdorferi 210 | 200 fg |
| 4, 19, 35 | B. burgdorferi 210 | 20 fg |
| 5, 20, 36 | B. burgdorferi 210 | 2 fg |
| 6, 21, 37 | B. burgdorferi 211 | $10^4$ copies |
| 7, 22, 38 | B. burgdorferi BPH11 (DN 1-2-7) | $10^4$ copies |
| 8, 23, 39 | B. hermsii 209 | $10^3$ copies |
| 9, 24, 40 | B. coriaceae | $1.5 \times 10^3$ copies |
| 10, 25, 41 | B. parkeri | $1.5 \times 10^3$ fg |
| 11, 26, 42 | B. turicatae | $1.5 \times 10^3$ fg |
| 12, 27, 43 | B. anserina | $1.5 \times 10^3$ fg |

1, 1E, 31 and 48 are molecular weight markers of φX174 cut with Hae III (New England Biolabs) 13–15, 28–30 and 44–46 are negative controls 32 and 47 are blank The sensitivity for the external "stand alone" primary amplification system (primers DD17 (SEQ ID No: 17) and DD18 (SEQ ID No: 18)) shown in Lanes 1–15 for *B. burgdorferi* is at 200 fg (Lane 3). Both European (211) and Californian (BPH11-DN 1-2-7) strains are amplified by these primers (Lanes 6 and 7). *B. hermsii* and *B. coriaceae* are weakly amplified (Lanes 8 and 9). *B. parkeri, B. turicatae* and *B. anserina* all amplify well with these primers (Lanes 10–12).

The sensitivity for the internal "stand alone" primary amplification system (primers DDl9 (SEQ ID No: 19)and DD20 (SEQ ID No: 20)) shown in Lanes 17–30 for *B. burgdorferi* DNA is at approximately 1 copy, 2 fg (Lanes 17–20). The primers amplify European (211 - Lane 21) and Californian (BPH11- DN 1-2-7 -Lane 22) strains well. *B. hermsii* and *B. coriaceae* show bands with moderate intensity (Lanes 23 and 24). *B. parkeri* and *B. turicatae* amplify well with these primers (Lanes 25 and 26). *B. anserina* was not amplified with these internal primers during primary amplification (Lane 27).

In the coamplification reaction using both sets of primers, the nested product (primer DD19 (SEQ. ID NO: 19) and DD20 (SEQ ID NO: 20)). {like on page 37, line 40–41} was produced for all Borrelia species tested. When the initial sample concentration was $10^3$ fg or lower, the nested product was preferentially produced over external product (Lanes 33–35, 39–43). When the initial sample concentration was above $10^3$ fg, more external product was produced whereas the internal, nested product was produced less efficiently (Lanes 37 and 38).

Example 7

Amplification of and Sequencing of *B. hermsii*

The primers DD02 (SEQ ID No: 2) and DD06 (SEQ ID No: 6) were used to amplify the 16S ribosomal RNA gene from *B. hermsii* and *B. burgdorferi*. The amplified products were subcloned into sequencing vectors as described in Maniatis Vol. 1 at Section 1.53.

From this reaction approximately 366 nucleotides of *B. hermsii* and *B. burgdorferi* were sequenced using the Sequenase kit and the instructions provided therein. The sequencing results are shown in FIG. 6. The *B. hermsii* sequence is shown in the middle line. The corresponding *B. burgdorferi* sequence, shown in the top line of FIG. 6, was aligned for maximum identity. As depicted in the bottom line of this figure, mismatches between the two species are shown. These regions of mismatch are advantageous for probe design.

Example 8

Sample Preparation for Direct Specimen Assay

For tick preparations, whole ticks (or the tick midgut) were crushed with sterile Pasteur pipets and suspended in 100 ul Tris buffer (10 mM Tris-HCl, 0.1 mM EDTA, pH 8.0). The solution was boiled at 100 ° C. for 15 min, spun in a microfuge for 5 min, and then the crude lysate was removed with a positive displacement pipet. Approximately 50 ml of the lysate is placed directly into the PCR reaction for amplification of the organism from the insect material.

Example 9

Preparation of Clinical Samples

The following protocols may be used to prepare DNA or RNA from blood cells or from tissue. To prepare the sample from blood cells, the procedure described by Kawasaki (see "Sample Preparation from Blood, Cells and Other Fluids" in *PCR Protocols, A Guide to Methods and Applications*, eds. Innis et al., Academic Press, 1990) is employed. Briefly, approximately 50 ul of whole blood from a patient suspected of having Lyme disease is mixed with 0.5 ml of TE in a 1.5 ml microfuge tube, which is then spun 0.5 ml of TE by vortexing and pelleted as before. This procedure is repeated twice more and the final pellet is resuspended in 100 ul of K buffer (PCR buffer without gelatin or BSA, containing 1% Laureth 12 or 0.5% Tween 20 and 100 ug/ml of fresh Proteinase K) and incubated as above. Approximately 10 ul of this solution is used in a PCR.

From a tissue sample, the tissue must first be homogenized employing standard procedures, and the homogenate is subjected to standard DNA isolation procedures (see for example, Maniatis et al., supra) to purify the DNA. The purified DNA is then used in a PCR.

Example 10

Detection of Target DNA in Cerebrospinal Fluid

Ten ul (direct addition) cerebrospinal fluid (CSF) added to 40 ul water and 50 ul Mastermix, were tested in a PCR with primers DD02 (SEQ ID No: 2) and DD06 (SEQ ID No: 6). The solution was heated first to 95° C. for 5 minutes followed by 50 cycles of a denaturing step at 95° C. for 25 seconds and an annealing step at 55° C. for 25 seconds. A final extension step was performed at 72° C. for 10 minutes, followed by a 10° C. soak overnight in the thermocycler.

The amplified DNA was immobolized on a nylon membrane and treated under prehybridizing conditions. About 10 pmoles of kinased probe DD04 (SEQ ID No: 4) was added to the membrane in solution and hybridization was ran for 3–5 hours at 60° C. The membrane was rinsed in 5× SSPE, 0.1% SDS at room temperature, washed in 2× SSPE, 0.1% SDS at 60° C. for 30 minutes followed by a wash in 0.2× SSPE, 0.1% SDS at 60° C. for 10 minutes. The blots were exposed to X-ray film and developed.

Out of nineteen patients tested, positive results were observed in nine patients who had been previously diagnosed with neuroborreliosis.

Example 11

Detection of Target DNA in Synovial Fluid

Two methods for sample preparation of synovial fluid have been evaluated. In the first method, 200 ul of synovial fluid were boiled at 100° C. for 5 minutes and the sample was centrifuged (16,000× g) for 30 minutes at 4° C. Approximately 10 ul of the supernatant were used in a 100 ul PCR reaction using. primers DD02 (SEQ ID No: 2) and DD06 (SEQ ID No: 6) followed by hybridization with probe DD04 (SEQ ID No: 4).

In the second method, 200 ul of synovial fluid was extracted with phenol: chloroform:isoamylalcohol (25:24:1) and the DNA precipitated with ethanol. About 10 ul of the extracted sample DNA was resuspended in 30 ul Tris-HCl, EDTA and used in a 100 ul PCR reaction with the same primers and probe identified above.

In this study, six patients were tested; three were diagnosed with Lyme arthritis, the other patients had different types of arthritis such osteoarthritis or rheumatoid arthritis. Positive results were observed using either sample preparation method in the three patients diagnosed with Lyme arthritis.

Example 12

Sample Preparation from Urine

About 1 ml of urine was added to a 1.5 ml microfuge tube and centrifuged (16,000×g) for 5 minutes at room temperature. The supernatant was removed and 250 ul sterile TE buffer was added to resuspend the pellet. The resuspended material was boiled at 100° C. for 10 minutes. The material was refrigerated at 4° C. until ready for use in PCR.

About 50 ul of the lysate was used in a PCR reaction employing the primers DD02 (SEQ ID No: 2) and DD06 (SEQ. ID No: 6), followed by detection with the probe DD04 (SEQ ID No: 4) as described for the CSF detection example. Using the "primary system" (50 cycles amplification followed by dot blot detection) for 36 samples, positive results were observed for a patient with early Lyme disease who had the *B. burgdorferi* specific ECM lesion (erythema chronicum migrans). A positive result was observed in 20 patients tested with early disease using the nested primer system (see Example 6 for conditions).

---

We claim:

1. A method for detecting if a Borrelia polynucleotide is contained in a sample, comprising:
  (a) carrying out a polymerase chain reaction in a mixture containing said sample and a pair of primers, wherein said pair of primers consists of DD02 (SEQ ID NO: 2) and a primer selected from the group consisting of
    DD03 (SEQ ID NO: 3),
    DD05 (SEQ ID NO: 5),
    DD06 (SEQ ID NO: 6), and
    DD07 (SEQ ID NO: 7), under conditions suitable for amplifying said polynucleotide to a detectable level;
  (b) contacting the product of step (a) with a probe under conditions under which said probe will form a stable hybrid duplex specifically with said polynucleotide, wherein said probe is selected from the group consisting of
    SEQ ID NO: 31,
    DD04 (SEQ ID NO: 4),
    DD15 (SEQ ID NO: 15),
    DD21 (SEQ ID NO: 21),
    DD23 (SEQ ID NO: 23),
    SEQ ID NO: 33,
    DD25 (SEQ ID NO: 29),
    DD27 (SEQ ID NO: 20), and
    the exact complements thereof; and
  (c) detecting if hybrid duplexes were formed, wherein the formation of hybrid duplexes indicates the presence of said polynucleotide.

2. A method of claim 1, wherein said pair of primers consists of DD02 (SEQ ID NO: 2) and DD06 (SEQ ID NO: 6).

3. A method of claim 1, wherein said probe is DD04 (SEQ ID NO: 4) or the exact complement thereof.

4. A method of claim 1, wherein said pair of primers consists of DD02 (SEQ ID NO: 2) and DD06 (SEQ ID NO: 6), and wherein said probe is DD04 (SEQ ID NO: 4) or the exact complement thereof.

5. An oligonucleotide probe that is DD04 (SEQ ID NO: 4) or the exact complement thereof.

6. A method for amplifying a Borrelia polynucleotide contained in a sample, comprising carrying out a polymerase chain reaction in a reaction mixture containing said sample and a pair of primers, wherein said pair of primers consists of DD02 (SEQ ID NO: 2) and a primer selected from the group consisting of

DD03 (SEQ ID NO: 3),

DD05 (SEQ ID NO: 5),

DD06 (SEQ ID NO: 6), and

DD07 (SEQ ID NO: 7), under conditions suitable for amplifying said polynucleotide to a detectable level.

7. The method of claim 6, wherein said pair of primers consists of DD02 (SEQ ID NO: 2) and DD06 (SEQ ID NO: 6).

8. A kit comprising a pair of primers, wherein said pair of primers consists of DD02 (SEQ ID NO: 2) and a primer selected from the group consisting of

DD03 (SEQ ID NO: 3),

DD05 (SEQ ID NO: 5),

DD06 (SEQ ID NO: 6), and

DD07 (SEQ ID NO: 7).

9. A kit of claim 8, wherein said pair of primers consists of DD02 (SEQ ID NO: 2) and DD06 (SEQ ID NO: 6).

10. A kit of claim 8, further comprising a probe, wherein said probe is selected from the group consisting of

SEQ ID NO: 31,

DD04 (SEQ ID NO: 4),

DD15 (SEQ ID NO: 15),

DD21 (SEQ ID NO: 21),

DD23 (SEQ ID NO: 23),

SEQ ID NO: 33,

DD25 (SEQ ID NO: 29),

DD27 (SEQ ID NO: 20), and the exact complements thereof.

11. A kit of claim 8, further comprising a probe, wherein said probe is DD04 (SEQ ID NO: 4) or the exact complement thereof.

12. A kit of claim 9, further comprising a probe, wherein said probe is selected from the group consisting of

SEQ ID NO: 31,

DD04 (SEQ ID NO: 4),

DD15 (SEQ ID NO: 15),

DD21 (SEQ ID NO: 21),

DD23 (SEQ ID NO: 23),

SEQ ID NO: 33,

DD25 (SEQ ID NO: 29),

DD27 (SEQ ID NO: 20), and the exact complements thereof.

13. A kit of claim 9, further comprising a probe, wherein said probe is DD04 (SEQ ID NO: 4) or the exact complement thereof.

* * * * *